(12) United States Patent
Choo et al.

(10) Patent No.: US 9,260,448 B2
(45) Date of Patent: Feb. 16, 2016

(54) THIENOPYRIMIDINONE DERIVATIVES AS MGLUR1 ANTAGONISTS

(71) Applicant: KOREA INSTITUTE OF SCIENCE AND TECHNOLOGY, Seoul (KR)

(72) Inventors: Hyunah Choo, Seoul (KR); Sun Joon Min, Seoul (KR); Seon Hee Seo, Seoul (KR); Jee Yeon Kim, Seoul (KR); Yoo Ran Ki, Seoul (KR); Min Joo Kim, Bucheon (KR); Sora Kim, Incheon (KR); Youngjae Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 52 days.

(21) Appl. No.: 14/038,324

(22) Filed: Sep. 26, 2013

(65) Prior Publication Data

US 2014/0228565 A1  Aug. 14, 2014

(30) Foreign Application Priority Data

Feb. 8, 2013 (KR) ........................ 10-2013-0014392

(51) Int. Cl.
*A01N 43/90* (2006.01)
*A61K 31/519* (2006.01)
*C07D 491/00* (2006.01)
*C07D 495/00* (2006.01)
*C07D 495/04* (2006.01)

(52) U.S. Cl.
CPC ............ *C07D 495/04* (2013.01); *A61K 31/519* (2013.01)

(58) Field of Classification Search
None
See application file for complete search history.

(56) References Cited

FOREIGN PATENT DOCUMENTS

WO     WO0004027     *  1/2000  ........... C07D 495/04

OTHER PUBLICATIONS

N. Bang et al., "Thrombolytic Therapy in Acute Myocardial Infarction," *Annual Review of Pharmacology and Toxicology*, vol. 29, 1989, pp. 323-341.
L. Martin et al., "Cellular Localization of Metabotropic Glutamate Receptor in Rat Brain," *Neuron*, vol. 9, Aug. 1992, pp. 259-270.
K. Fisher et al., "Comparison of Nociceptive Effects Produced by Intrathecal Administration of mGluR Agonists," *NeuroReport*, vol. 7, 1996, pp. 2743-2747.
F. Bordi et al., "Group I Metabotropic Glutamate Receptors: Implications for Brain Diseases," *Progress in Neurobiology*, vol. 59, 1999, pp. 55-79.
F. Karim et al., "Metabotropic Glutamate Receptor Subtypes 1 and 5 Are Activators of Extracellular Signal-Regulated Kinase Signaling Required for Inflammatory Pain in Mice," *The Journal of Neuroscience*, vol. 21, No. 11, Jun. 2001, pp. 3771-3779.
V. Neugebauer, "Peripheral Metabotropic Glutamate Receptor: Fight the Pain Where it Hurts," *Trends in Neurosciences*, vol. 24, No. 10, Oct. 2001, pp. 550-552.
V. Neugebauer et al., "Peripheral Metabotropic Glutamate Receptors as Drug Targets for Pain Relief," *Expert Opinion Therapy Targets*, vol. 6, No. 3, 2002, pp. 349-361.

* cited by examiner

*Primary Examiner* — Jeffrey H Murray
(74) *Attorney, Agent, or Firm* — Goldilocks Zone IP Law

(57) ABSTRACT

Disclosed are thienopyrimidinone derivatives as antagonists that act on metabotropic glutamate receptor subtype 1. The thienopyrimidinone derivatives show pharmacological activity against metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease. Also disclosed are methods for preparing the thienopyrimidinone derivatives, and pharmaceutical compositions containing the thienopyrimidinone derivatives as active ingredients.

13 Claims, 6 Drawing Sheets

| Comp. | Structure | Comp. | Structure |
|---|---|---|---|
| 1 |  KDDG00346 | 10 |  KDDG00310 |
| 2 |  KDDG00299 | 11 |  KDDG00179 |
| 3 |  KDDG00267 | 12 |  KDDG00127 |
| 4 |  KDDG00128 | 13 |  KDDG00202 |
| 5 |  KDDG00300 | 14 |  KDDG00204 |
| 6 |  KDDG00266 | 15 |  KDDG00258 |
| 7 |  KDDG00126 | 16 |  KDDG00309 |
| 8 |  KDDG00311 | 17 |  KDDG00312 |
| 9 |  KDDG00314 | 18 |  KDDG00178 |

FIG. 2

| | | | | |
|---|---|---|---|---|
| 19 | KDDG00200 | 29 | KDDG00265 |
| 20 | KDDG00203 | 30 | KDDG00349 |
| 21 | KDDG00205 | 31 | KDDG00148 |
| 22 | KDDG00201 | 32 | KDDG00146 |
| 23 | KDDG00347 | 33 | KDDG00145 |
| 24 | KDDG00348 | 34 | KDDG00259 |
| 25 | KDDG00313 | 35 | KDDG00350 |
| 26 | KDDG00230 | 36 | KDDG00350 |
| 27 | KDDG00316 | 37 | KDDG00351 |
| 28 | KDDG00317 | 38 | KDDG00352 |

FIG. 3

| | | | | |
|---|---|---|---|---|
| 39 | KDDG00353 | 49 | KDDG00185 |
| 40 | KDDG00354 | 50 | KDDG00135 |
| 41 | KDDG00199 | 51 | KDDG00306 |
| 42 | KDDG00182 | 52 | KDDG00307 |
| 43 | KDDG00181 | 53 | KDDG00308 |
| 44 | KDDG00184 | 54 | KDDG00322 |
| 45 | KDDG00183 | 55 | KDDG00323 |
| 46 | KDDG00326 | 56 | KDDG00330 |
| 47 | KDDG00327 | 57 | KDDG00331 |
| 48 | KDDG00186 | 58 | KDDG00229 |

FIG. 4

| | | | |
|---|---|---|---|
| 59 | KDDG00228 | 69 | KDDG00303 |
| 60 | KDDG00324 | 70 | KDDG00318 |
| 61 | KDDG00325 | 71 | KDDG00319 |
| 62 | KDDG00328 | 72 | KDDG00302 |
| 63 | KDDG00329 | 73 | KDDG00301 |
| 64 | KDDG00334 | 74 | KDDG00297 |
| 65 | KDDG00335 | 75 | KDDG00136 |
| 66 | KDDG00320 | 76 | KDDG00147 |
| 67 | KDDG00321 | 77 | KDDG00366 |
| 68 | KDDG00304 | 78 | KDDG00383 |

| 79 |  KDDG00367 | 89 |  KDDG00381 |
|---|---|---|---|
| 80 |  KDDG00362 | 90 |  KDDG00382 |
| 81 |  KDDG00363 | 91 |  KDDG00425 |
| 82 |  KDDG00364 | 92 |  KDDG00426 |
| 83 |  KDDG00368 | 93 |  KDDG00427 |
| 84 |  KDDG00369 | 94 |  KDDG00428 |
| 85 |  KDDG00365 | 95 |  KDDG00429 |
| 86 |  KDDG00378 | 96 |  KDDG00430 |
| 87 |  KDDG00379 | 97 |  KDDG00440 |
| 88 |  KDDG00380 | 98 |  KDDG00431 |

| 99 |  KDDG00432 | 109 |  KDDG00264 |
|---|---|---|---|
| 100 |  KDDG00433 | 110 |  KDDG00444 |
| 101 |  KDDG00434 | 111 |  KDDG00445 |
| 102 |  KDDG00435 | 112 |  KDDG00446 |
| 103 |  KDDG00436 | 113 |  KDDG00447 |
| 104 |  KDDG00437 | 114 |  KDDG00448 |
| 105 |  KDDG00438 | 115 |  KDDG00449 |
| 106 |  KDDG00439 | 116 |  KDDG00450 |
| 107 |  KDDG00177 | 117 |  KDDG00451 |
| 108 |  KDDG00180 | | |

THIENOPYRIMIDINONE DERIVATIVES AS MGLUR1 ANTAGONISTS

CROSS-REFERENCE TO RELATED APPLICATIONS

This application claims priority under 35 U.S.C. §119 to Korean Patent Application No. 10-2013-0014392 filed on Feb. 8, 2013, in the Korean Intellectual Property Office, the disclosure of which is incorporated herein by reference in its entirety.

BACKGROUND OF THE INVENTION

1. Field of the Invention

The present invention relates to thienopyrimidinone derivatives as antagonists that act on metabotropic glutamate receptor subtype 1 to show pharmacological activity against metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease. The present invention also relates to methods for preparing the compounds, and pharmaceutical compositions containing the compounds as active ingredients.

2. Description of the Related Art

Glutamate is an important excitatory neurotransmitter in the central nervous system. Synaptic stimulation of glutamate is transmitted through the activities of two receptor types: ionotropic glutamate receptors and metabotropic glutamate receptors. The former receptors are ligand-gated cation channels, and the latter receptors are G-protein-coupled receptors (GPCRs). Metabotropic glutamate receptors are divided into three groups on the basis of their structural similarity, pharmacology, and signaling mechanisms. The three groups are further subdivided into a total of eight subtypes according to their splicing variants. The group I receptors are divided into mGluR1 and mGluR5. The subtypes mGluR1 and mGluR5 activate phospholipase C (PLC) via a Gq/11 protein, resulting in release of calcium via phosphoinositide (PI) hydrolysis. The group II receptors (mGluR2 and mGluR3) and the group III receptors (mGluR4, mGluR5, mGluR6, and mGluR7) are negatively coupled to adenyl cyclase (AC) via a Gi/o protein, inhibiting cAMP formation.

Approximately 70 million Americans suffer from pain. The annual medical expenses for pain treatment and related social costs in the United States are estimated to be 100 billion dollars. Neuropathic pain has numerous etiologies and causes complex and chronic pain conditions. A total of about 18 million Americans, including about 4 million Americans suffering from diabetic pain, are afflicted with neuropathic pain. Various neurological diseases including pain, psychiatric diseases and neuritic diseases are associated with glutamate release. mGluR1, a glutamate receptor, is present on the primary afferent nerve terminals and is abundantly distributed in the pain process-related nervous tissues of the CNS. Thus, mGluR1 is reported to be closely associated with the treatment of pain [Annu. Rev. Pharmacol. Toxicol. 1989, 29, 365; Trends Neurosci. 2011, 24, 550; Expert Opin. Ther. Targets 2002, 6, 349; Neuron 1992, 9, 259].

Various experiment results have revealed that mGluR1 antagonism relieves neuropathic pain. It was reported that the injection of selective mGluR1 antibodies relieves allodynia and hyperalgesia in animal models, and the administration of selective mGluR1 antagonists after administration of Group I mGluR agonists to induce spontaneous pain relieves the pain [Prog. Neurobiol. 1999, 59, 55; Neuro-Report 1996, 7, 2743; J. Neurosci. 2001, 21. 3771].

Many efforts have been made to date to develop mGluR1 antagonists. However, there is still a need for mGluR1 antagonists that are selective for mGluR1, have good pharmacokinetic profiles, have good absorption, distribution, metabolism and excretion (ADME) properties, and are effective against metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease.

SUMMARY OF THE INVENTION

It is an object of the present invention to provide novel compounds as mGluR1 modulators that are effective against metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease.

Specifically, it is an object of the present invention to provide thienopyrimidinone derivatives having novel structures and pharmaceutically acceptable salts thereof.

It is a further object of the present invention to provide methods for preparing thienopyrimidinone derivatives from 4-aryl-3-amino-2-alkoxycarbonylthiophenes, which are prepared from arylmethylcyanides through three steps.

It is another object of the present invention to provide pharmaceutical compositions acting on mGluR1, each of the compositions including at least one of the thienopyrimidinone derivatives and pharmaceutically acceptable salts thereof as an active ingredient.

It is still another object of the present invention to provide drugs for the prevention and treatment of pain, such as neuropathic pain and migraine, psychiatric diseases, such as anxiety disorder and schizophrenia, urinary incontinence, and neurodegenerative diseases, such as Parkinson's disease and Alzheimer's disease, each of the drugs including at least one of the thienopyrimidinone derivatives and pharmaceutically acceptable salts as an active ingredient.

According to one aspect of the present invention, there is provided a thienopyrimidinone derivative effective as a compound that acts on mGluR1 to show efficacy against metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease, wherein the thienopyrimidinone derivative is represented by Formula 1:

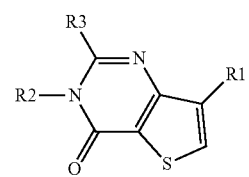

(1)

wherein R1 represents an aryl group, R2 represents an alkyl or aryl group, and R3 represents a hydrogen atom, a hydroxyl group, an alkyl group, or an alkylamine group.

According to another aspect of the present invention, there is provided a method for preparing the thienopyrimidinone derivative.

According to yet another aspect of the present invention, there is provided a pharmaceutical composition including the thienopyrimidinone derivative.

The thienopyrimidinone derivative of Formula 1 or pharmaceutically acceptable salt thereof according to the present invention exhibits excellent activity as compounds acting on mGluR1, thus being useful as a therapeutic or prophylactic agent for metabotropic glutamate receptor-related diseases, including pain, such as neuropathic pain and migraine, psychiatric diseases, such as anxiety disorder and schizophrenia, urinary incontinence, and neurodegenerative diseases, such as Parkinson's disease and Alzheimer's disease.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1 to 6 show the structures of compounds according to embodiments of the present invention.

DETAILED DESCRIPTION OF THE INVENTION

Figure 1:
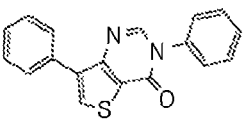
Figure 1:
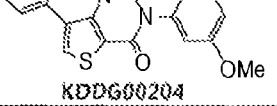
Figure 1:
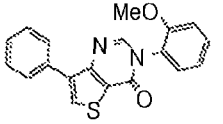
Figure 1:
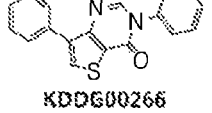
Figure 1:
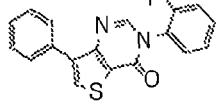
Figure 1:
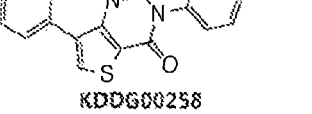
Figure 1:
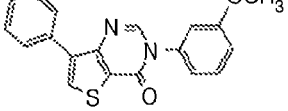
Figure 1:
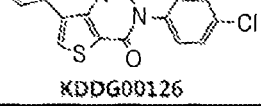
Figure 1:
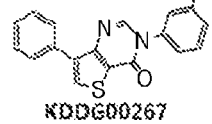
Figure 1:
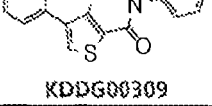
Figure 1:
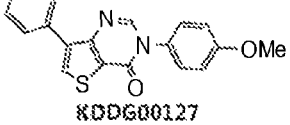
Figure 1:
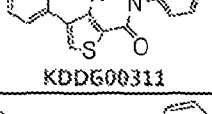
Figure 1:
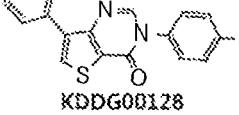
Figure 1:
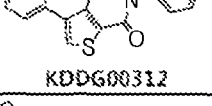
Figure 1:
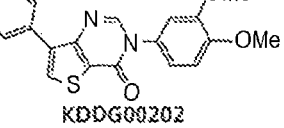
Figure 1:
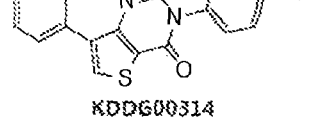
Figure 1:
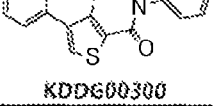
Figure 1:
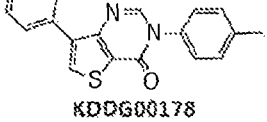
Figure 5:
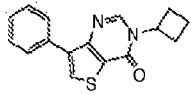
Figure 5:
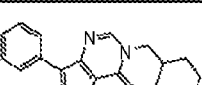
Figure 5:
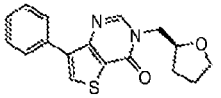
Figure 5:
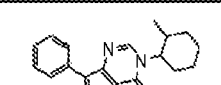
Figure 5:
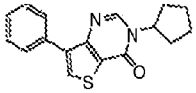
Figure 5:
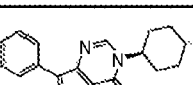
Figure 5:
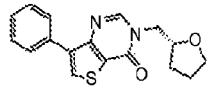
Figure 5:
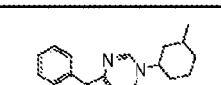
Figure 5:
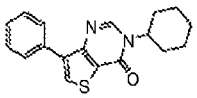
Figure 5:
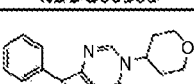
Figure 5:
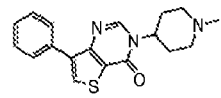
Figure 5:
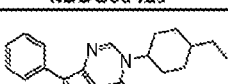
Figure 5:
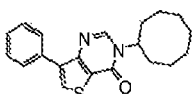
Figure 5:
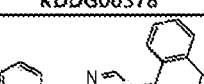
Figure 5:
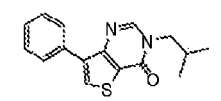
Figure 5:
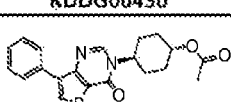
Figure 5:
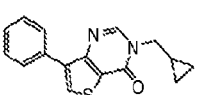
Figure 5:
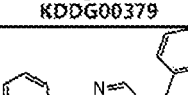
Figure 5:
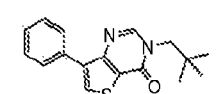
Figure 5:
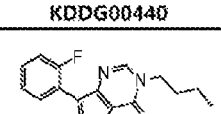
Figure 6:
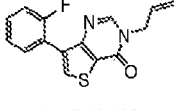
Figure 6:
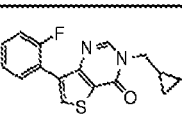
Figure 6:
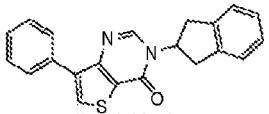
Figure 6:
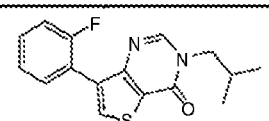
Figure 6:
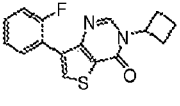
Figure 6:
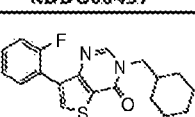
Figure 6:
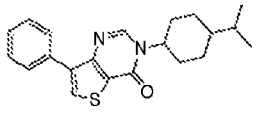
Figure 6:
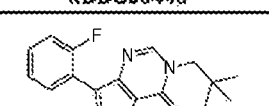
Figure 6:
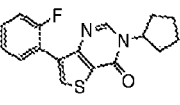
Figure 6:
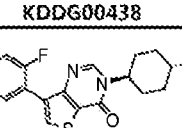
Figure 6:
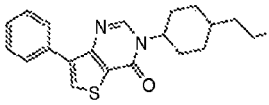
Figure 6:
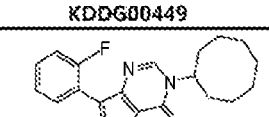
Figure 6:
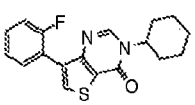
Figure 6:
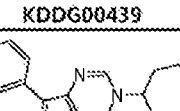
Figure 6:
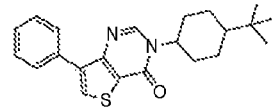
Figure 6:
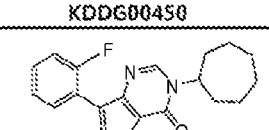
Figure 6:
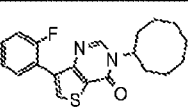
Figure 6:
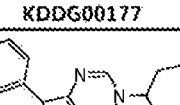
Figure 6:
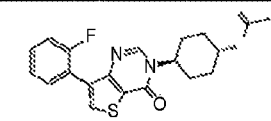

Aspects and embodiments of the present invention will now be described in more detail.

In one aspect, the present invention provides a thienopyrimidinone derivative represented by Formula 1:

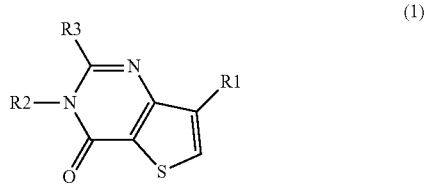

(1)

wherein R1 is phenyl which is unsubstituted or substituted with one to five substituents selected from halogen, substituted or unsubstituted stannyl, phenyl, alkylphenyl, alkoxyphenyl, benzodioxolyl, and naphthalenyl groups, R2 is selected from substituted or unsubstituted phenyl, substituted or unsubstituted $C_1$-$C_7$ alkyl, substituted or unsubstituted $C_3$-$C_{10}$ cycloalkyl, pyranyl, hydropyranyl, naphthalenyl, hydronaphthalenyl, substituted or unsubstituted piperidinyl, acetyloxy, allyl, and vinyl, and R3 is selected from hydrogen, $C_1$-$C_7$ alkyl, substituted or unsubstituted amino, and hydroxy; or a pharmaceutically acceptable salt thereof.

In the case where R3 is a hydroxyl group, tautomeric isomerism (tautomerism) may occur. In this case, the thienopyrimidinone derivative of Formula 1 may also exist in a tautomeric form represented by Formula 2:

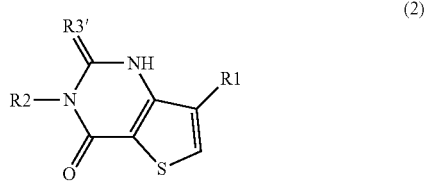

(2)

wherein R1 and R2 are as defined in Formula 1, and R3' is oxygen.

It is therefore to be understood that the tautomeric form of Formula 2 is within the scope of the present invention.

In one embodiment, R1 is selected from substituted or unsubstituted phenyl, substituted or unsubstituted naphthalenyl, and substituted or unsubstituted benzodioxolyl.

The substituted phenyl may be phenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, substituted or unsubstituted stannyl, and phenyl.

The substituted stannyl may be alkylstannyl substituted with one to three $C_1$-$C_7$ alkyl groups.

The substituted naphthalenyl may be naphthalenyl in which some or all of the hydrogen atoms are replaced by substituents selected from halogen, $C_1$-$C_7$ alkyl, $C_1$-$C_7$ alkoxy, unsubstituted stannyl, $C_1$-$C_7$ alkylstannyl, $C_1$-$C_7$ dialkylstannyl, $C_1$-$C_7$ trialkylstannyl, and phenyl.

The substituted benzodioxolyl may be benzodioxolyl in which some or all of the hydrogen atoms are replaced by substituents selected from halogen, $C_1$-$C_7$ alkyl, $C_1$-$C_7$ alkoxy, unsubstituted stannyl, $C_1$-$C_7$ alkylstannyl, $C_1$-$C_7$ dialkylstannyl, $C_1$-$C_7$ trialkylstannyl, and phenyl.

In a further embodiment, (i) R2 may be selected from substituted or unsubstituted phenyl, substituted or unsubstituted benzonitrile, substituted or unsubstituted $C_1$-$C_7$ alkyl, allyl, vinyl, substituted or unsubstituted $C_3$-$C_{10}$ cycloalkyl, substituted or unsubstituted pyranyl, substituted or unsubstituted hydropyranyl, substituted or unsubstituted naphthalenyl, substituted or unsubstituted hydronaphthalenyl, substituted or unsubstituted furanyl, substituted or unsubstituted hydrofuranyl, substituted or unsubstituted piperidinyl, and substituted or unsubstituted $C_3$-$C_{10}$ heterocycloalkyl; or (ii) R2 may have a $C_1$-$C_7$ alkyl group through which a group selected from substituted or unsubstituted phenyl, substituted or unsubstituted benzonitrile, substituted or unsubstituted $C_1$-$C_7$ alkyl, allyl, vinyl, substituted or unsubstituted $C_3$-$C_{10}$ cycloalkyl, substituted or unsubstituted pyranyl, substituted or unsubstituted hydropyranyl, substituted or unsubstituted naphthalenyl, substituted or unsubstituted hydronaphthalenyl, substituted or unsubstituted furanyl, substituted or unsubstituted hydrofuranyl, substituted or unsubstituted piperidinyl, and substituted or unsubstituted $C_3$-$C_{10}$ heterocycloalkyl is linked to the corresponding nitrogen atom of the thienopyrimidinone ring.

The substituted phenyl may be phenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The substituted benzonitrile may be benzonitrile in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The substituted $C_1$-$C_7$ alkyl may be $C_1$-$C_7$ alkyl in which one to three hydrogen atoms of the alkyl are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, allyl, $C_3$-$C_{10}$ cycloalkyl, furanyl, and hydrofuranyl.

The substituted $C_3$-$C_{10}$ cycloalkyl may be $C_3$-$C_{10}$ cycloalkyl substituted with substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, allyl, and $C_1$-$C_7$ alkyl.

The substituted pyranyl may be pyranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The hydropyranyl may be dihydropyranyl or tetrahydropyranyl, and the substituted hydropyranyl may be hydropyranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The substituted naphthalenyl may be naphthalenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The hydronaphthalenyl may be selected from dihydronaphthalenyl, tetrahydronaphthalenyl, hexahydronaphthalenyl, and heptahydronaphthalenyl, and the substituted hydronaphthalenyl may be hydronaphthalenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The substituted furanyl may be furanyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The hydrofuranyl may be dihydrofuranyl or tetrahydrofuranyl, and the substituted hydrofuranyl may be hydrofuranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

The substituted piperidinyl may be (i) piperidinyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl, or (ii) piperidinyl in which a substituent selected from $C_1$-$C_7$ alkyl, halogenated $C_1$-$C_7$ alkyl, $C_1$-$C_7$ alkoxy, halogenated $C_1$-$C_7$ alkoxy, vinyl, and allyl is bonded to the nitrogen atom of the piperidine ring.

The $C_3$-$C_{10}$ heterocycloalkyl may be heterocycloalkyl in which one or two heteroatoms selected from N, O and S, and three to ten carbon atoms are bonded together to form a ring; and the substituted $C_3$-$C_{10}$ heterocycloalkyl may be heterocycloalkyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

In one embodiment, the substituted phenyl in R1 is phenyl substituted with one to five substituents selected from halogen, substituted or unsubstituted stannyl, phenyl, alkylphenyl, alkoxyphenyl, benzodioxolyl, and naphthalenyl; the substituted stannyl in R1 is stannyl substituted with one to three $C_1$-$C_7$ alkyl groups; the alkylphenyl in R1 is phenyl substituted with $C_1$-$C_7$ alkyl; the alkoxyphenyl in R1 is phenyl substituted with $C_1$-$C_7$ alkoxy; and the substituted phenyl in R2 is phenyl substituted with one to five substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, allyl, and benzonitrile.

In a further embodiment, the substituted $C_1$-$C_7$ alkyl in R2 is $C_1$-$C_7$ alkyl substituted with at least one substituent selected from $C_3$-$C_{10}$ cycloalkyl, furanyl, and hydrofuranyl; the hydrofuranyl is dihydrofuranyl or tetrahydrofuranyl; the substituted $C_3$-$C_{10}$ cycloalkyl in R2 is $C_3$-$C_{10}$ cycloalkyl substituted with $C_1$-$C_7$ alkyl; the hydropyranyl in R2 is dihydropyranyl or tetrahydropyranyl; the hydronaphthalenyl in R2 is selected from dihydronaphthalenyl, tetrahydronaphthalenyl, hexahydronaphthalenyl, and heptahydronaphthalenyl; and the substituted piperidinyl in R2 is piperidinyl substituted with at least one $C_1$-$C_7$ alkyl group.

The phenyl substituted with benzonitrile is phenyl substituted with a substituent having any one of the structures of Formulae 3 to 5:

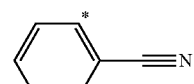

(3)

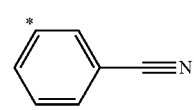

(4)

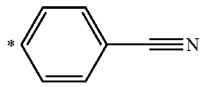

(5)

wherein each asterisk (*) indicates a position where phenyl is bonded.

The substituted amino in R3 is amino substituted with one or two $C_1$-$C_7$ alkyl groups.

In another embodiment, R1 is selected from phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trimethylstannylphenyl, 3-trimethylstannylphenyl, 4-trimethylstannylphenyl, 2-methylphenyl, 3-methylphenyl, 4-methylphenyl, 2-methoxyphenyl, 3-methoxyphenyl, 4-methoxyphenyl, 3,4-dimethoxyphenyl, 4-benzodioxolyl, 5-benzodioxolyl, 1-naphthalenyl, and 2-naphthalenyl.

In another embodiment, R2 is selected from phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-methoxyphenyl, 3-methoxyphenyl, 4-methoxyphenyl, 3,4-dimethoxyphenyl, 3,5-dimethoxyphenyl, 2-hydroxyphenyl, 3-hydroxyphenyl, 4-hydroxyphenyl, 2-methylphenyl, 3-methylphenyl, 4-methylphenyl, 2,5-dimethylphenyl, 2,6-dimethylphenyl, 3,4-dimethylphenyl, benzonitrile, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-nitrophenyl, 3-nitrophenyl, 4-nitrophenyl, 2-vinylphenyl, 3-vinylphenyl, 4-vinylphenyl, butyl, allyl, cyclobutyl, cyclopentyl, cyclohexyl, cyclooctyl, cyclopropylmethyl, cyclohexylmethyl, 4-methylcyclohexyl, tetrahydropyran-4-yl, 1,2,3,4-tetrahydronaphthalen-1-yl, tetrahydrofuran-2-ylmethyl, 1-methylpiperidin-4-yl, isobutyl, neopentyl, 2-methylcyclohexyl, 3-methylcyclohexyl, 4-ethylcyclohexyl, and acetyloxy.

In another embodiment, R3 is selected from hydrogen, methyl, and dimethylamino.

In another embodiment, the thienopyrimidinone derivative is any one of the following compounds:
3,7-diphenylthieno[3,2-d]pyrimidin-4(3H)-one;
3-(2-fluorophenyl)-7-phenylthieno[3,2-d]pyrimidin-4(3H)-one;

3-(3-fluorophenyl)-7-phenylthieno[3,2-d]pyrimidin-4(3H)-one;
3-(4-fluorophenyl)-7-phenylthieno[3,2-d]pyrimidin-4(3H)-one;
3-(2-chlorophenyl)-7-phenylthieno[3,2-d]pyrimidin-4(3H)-one;
3-(3-chlorophenyl)-7-phenylthieno[3,2-d]pyrimidin-4(3H)-one;
3-(4-chlorophenyl)-7-phenylthieno[3,2-d]pyrimidin-4(3H)-one;
3-(3-bromophenyl)-7-phenylthieno[3,2-d]pyrimidin-4(3H)-one;
3-(4-bromophenyl)-7-phenylthieno[3,2-d]pyrimidin-4(3H)-one;
3-(2-methoxyphenyl)-7-phenylthieno[3,2-d]pyrimidin-4(3H)-one;
3-(3-methoxyphenyl)-7-phenylthieno[3,2-d]pyrimidin-4(3H)-one;
3-(4-methoxyphenyl)-7-phenylthieno[3,2-d]pyrimidin-4(3H)-one;
3-(3,4-dimethoxyphenyl)-7-phenylthieno[3,2-d]pyrimidin-4(3H)-one;
3-(3,5-dimethoxyphenyl)-7-phenylthieno[3,2-d]pyrimidin-4(3H)-one;
3-(4-hydroxyphenyl)-7-phenylthieno[3,2-d]pyrimidin-4(3H)-one;
7-phenyl-3-(o-tolyl)thieno[3,2-d]pyrimidin-4(3H)-one;
7-phenyl-3-(m-tolyl)thieno[3,2-d]pyrimidin-4(3H)-one;
7-phenyl-3-p-tolylthieno[3,2-d]pyrimidin-4(3H)-one;
3-(4-ethylphenyl)-7-phenylthieno[3,2-d]pyrimidin-4(3H)-one;
3-(2,6-dimethylphenyl)-7-phenylthieno[3,2-d]pyrimidin-4(3H)-one;
3-(2,5-dimethylphenyl)-7-phenylthieno[3,2-d]pyrimidin-4(3H)-one;
3-(3,4-dimethylphenyl)-7-phenylthieno[3,2-d]pyrimidin-4(3H)-one;
3-(4-oxo-7-phenylthieno[3,2-d]pyrimidin-3(4H)-yl)benzonitrile;
4-(4-oxo-7-phenylthieno[3,2-d]pyrimidin-3(4H)-yl)benzonitrile;
7-phenyl-3-(3-trifluoromethyl)phenyl)thieno[3,2-d]pyrimidin-4(3H)-one;
7-phenyl-3-(4-(trifluoromethyl)phenyl)thieno[3,2-d]pyrimidin-4(3H)-one;
7-phenyl-3-(4-trifluoromethoxy)phenyl)thieno[3,2-d]pyrimidin-4(3H)-one;
3-(4-nitrophenyl)-7-phenylthieno[3,2-d]pyrimidin-4(3H)-one;
7-phenyl-3-(3-vinylphenyl)thieno[3,2-d]-pyrimidin-4(3H)-one;
7-phenyl-3-(4-vinylphenyl)thieno[3,2-d]pyrimidin-4(3H)-one;
3-(4-fluorophenyl)-7-(2-fluorophenyl)thieno[3,2-d]pyrimidin-4(3H)-one;
3-(4-chlorophenyl)-7-(2-fluorophenyl)thieno[3,2-d]pyrimidin-4(3H)-one;
7-(2-fluorophenyl)-3-(4-methoxyphenyl)thieno[3,2-d]pyrimidin-4(3H)-one;
7-(2-fluorophenyl)-3-(4-hydroxyphenyl)thieno[3,2-d]pyrimidin-4(3H)-one;
7-(2-fluorophenyl)-3-(3-hydroxyphenyl)thieno[3,2-d]pyrimidin-4(3H)-one;
7-(2-fluorophenyl)-3-(m-tolyl)thieno[3,2-d]pyrimidin-4(3H)-one;
3-(3-chlorophenyl)-7-(2-fluorophenyl)thieno[3,2-d]pyrimidin-4(3H)-one;
7-(2-fluorophenyl)-3-(3-vinylphenyl)thieno[3,2-d]pyrimidin-4(3H)-one;
3-(7-(2-fluorophenyl)-4-oxothieno[3,2-d]pyrimidin-3(4H)-yl)benzonitrile;
3-(4-chlorophenyl)-7-(3-fluorophenyl)thieno[3,2-d]pyrimidin-4(3H)-one;
7-(3-fluorophenyl)-3-(4-methoxyphenyl)thieno[3,2-d]pyrimidin-4(3H)-one;
3-(4-chlorophenyl)-7-(4-fluorophenyl)thieno[3,2-d]pyrimidin-4(3H)-one;
7-(4-fluorophenyl)-3-(4-methoxyphenyl)thieno[3,2-d]pyrimidin-4(3H)-one;
7-(2-chlorophenyl)-3-(4-chlorophenyl)thieno[3,2-d]pyrimidin-4(3H)-one;
7-(2-chlorophenyl)-3-(4-methoxyphenyl)thieno[3,2-d]pyrimidin-4(3H)-one;
7-(3-chlorophenyl)-3-(4-chlorophenyl)thieno[3,2-d]pyrimidin-4(3H)-one;
7-(3-chlorophenyl)-3-(4-methoxyphenyl)thieno[3,2-d]pyrimidin-4(3H)-one;
3,7-bis(4-chlorophenyl)thieno[3,2-d]pyrimidin-4(3H)-one;
7-(4-chlorophenyl)-3-(4-methoxyphenyl)thieno[3,2-d]pyrimidin-4(3H)-one;
7-(2-bromophenyl)-3-(4-chlorophenyl)thieno[3,2-d]pyrimidin-4(3H)-one;
7-(2-bromophenyl)-3-(4-methoxyphenyl)thieno[3,2-d]pyrimidin-4(3H)-one;
7-(2-iodophenyl)-3-(4-methoxyphenyl)thieno[3,2-d]pyrimidin-4(3H)-one;
3-(4-methoxyphenyl)-7-(2-(trimethylstannyl)phenyl)thieno[3,2-d]pyrimidin-4(3H)-one;
3-(4-chlorophenyl)-7-(o-tolyl)thieno[3,2-d]pyrimidin-4(3H)-one;
3-(4-methoxyphenyl)-7-(o-tolyl)thieno[3,2-d]pyrimidin-4(3H)-one;
3-(4-chlorophenyl)-7-(m-tolyl)thieno[3,2-d]pyrimidin-4(3H)-one;
3-(4-methoxyphenyl)-7-(m-tolyl)thieno[3,2-d]pyrimidin-4(3H)-one;
3-(4-chlorophenyl)-7-(p-tolyl)thieno[3,2-d]pyrimidin-4(3H)-one;
3-(4-methoxyphenyl)-7-(p-tolyl)thieno[3,2-d]pyrimidin-4(3H)-one;
3-(4-chlorophenyl)-7-(2-methoxyphenyl)thieno[3,2-d]pyrimidin-4(3H)-one;
7-(2-methoxyphenyl)-3-(4-methoxyphenyl)thieno[3,2-d]pyrimidin-4(3H)-one;
3-(4-chlorophenyl)-7-(3-methoxyphenyl)thieno[3,2-d]pyrimidin-4(3H)-one;
7-(3-methoxyphenyl)-3-(4-methoxyphenyl)thieno[3,2-d]pyrimidin-4(3H)-one;
3-(4-chlorophenyl)-7-(4-methoxyphenyl)thieno[3,2-d]pyrimidin-4(3H)-one;
3,7-bis(4-methoxyphenyl)thieno[3,2-d]pyrimidin-4(3H)-one;
3-(4-chlorophenyl)-7-(3,4-dimethoxyphenyl)thieno[3,2-d]pyrimidin-4(3H)-one;
7-(3,4-dimethoxyphenyl)-3-(4-methoxyphenyl)thieno[3,2-d]pyrimidin-4(3H)-one;
7-(benzo[d][1,3]dioxol-5-yl)-3-(4-chlorophenyl)thieno[3,2-d]pyrimidin-4(3H)-one;
7-(benzo[d][1,3]dioxol-5-yl)-3-(4-methoxyphenyl)thieno[3,2-d]pyrimidin-4(3H)-one;
3-(4-chlorophenyl)-7-(naphthalen-1-yl)-3,4-dihydrothieno[3,2-d]pyrimidin-4(3H)-one;
3-(4-methoxyphenyl)-7-(naphthalen-1-yl)-3,4-dihydrothieno[3,2-d]pyrimidin-4(3H)-one;
3-(4-chlorophenyl)-7-(naphthalen-2-yl)-3,4-dihydrothieno[3,2-d]pyrimidin-4(3H)-one;
3-(4-methoxyphenyl)-7-(naphthalen-2-yl)-3,4-dihydrothieno[3,2-d]pyrimidin-4(3H)-one;

3-(4-methoxyphenyl)-2-methyl-7-phenylthieno[3,2-d]pyrimidin-4(3H)-one;
3-(4-chlorophenyl)-7-phenylthieno[3,2-d]pyrimidin-2,4(1H,3H)-dione;
3-(4-chlorophenyl)-2-(dimethylamino)-7-phenylthieno[3,2-d]pyrimidin-4(3H)-one;
3-butyl-7-phenylthieno[3,2-d]pyrimidin-4(3H)-one;
3-allyl-7-phenylthieno[3,2-d]pyrimidin-4(3H)-one;
3-cyclobutyl-7-phenylthieno[3,2-d]pyrimidin-4(3H)-one;
3-cyclopentyl-7-phenylthieno[3,2-d]pyrimidin-4(3H)-one;
3-cyclohexyl-7-phenylthieno[3,2-d]pyrimidin-4(3H)-one;
3-cyclooctyl-7-phenylthieno[3,2-d]pyrimidin-4(3H)-one;
3-(cyclopropylmethyl)-7-phenylthieno[3,2-d]pyrimidin-4(3H)-one;
3-(cyclohexylmethyl)-7-phenylthieno[3,2-d]pyrimidin-4(3H)-one;
3-((1R,4R)-4-methylcyclohexyl)-7-phenylthieno[3,2-d]pyrimidin-4(3H)-one;
7-phenyl-3-(tetrahydro-2H-pyran-4-yl)thieno[3,2-d]pyrimidin-4(3H)-one;
(R)-7-phenyl-3-(1,2,3,4-tetrahydronaphthalen-1-yl)thieno[3,2-d]pyrimidin -4(3H)-one;
(S)-7-phenyl-3-(1,2,3,4-tetrahydronaphthalen-1-yl)thieno[3,2-d]pyrimidin -4(3H)-one;
(S)-7-phenyl-3-((tetrahydrofuran-2-yl)methyl)thieno[3,2-d]pyrimidin-4(3H)-one;
(R)-7-phenyl-3-((tetrahydrofuran-2-yl)methyl)thieno[3,2-d]pyrimidin-4(3H)-one;
3-(1-methylpiperidin-4-yl)-7-phenylthieno[3,2-d]pyrimidin-4(3H)-one;
3-isobutyl-7-phenylthieno[3,2-d]pyrimidin-4(3H)-one;
3-neopentyl-7-phenylthieno[3,2-d]pyrimidin-4(3H)-one;
3-(2-methylcyclohexyl)-7-phenylthieno[3,2-d]pyrimidin-4(3H)-one;
3-(3-methylcyclohexyl)-7-phenylthieno[3,2-d]pyrimidin-4(3H)-one;
3-(4-ethylcyclohexyl)-7-phenylthieno[3,2-d]pyrimidin-4(3H)-one;
(1R,4R)-4-(4-oxo-7-phenylthieno[3,2-d]pyrimidin-3(4H)-yl)cyclohexyl acetate;
3-butyl-7-(2-fluorophenyl)thieno[3,2-d]pyrimidin-4(3H)-one;
3-allyl-7-(2-fluorophenyl)thieno[3,2-d]pyrimidin-4(3H)-one;
3-cyclobutyl-7-(2-fluorophenyl)thieno[3,2-d]pyrimidin-4(3H)-one;
3-cyclopentyl-7-(2-fluorophenyl)thieno[3,2-d]pyrimidin-4(3H)-one;
3-cyclohexyl-7-(2-fluorophenyl)thieno[3,2-d]pyrimidin-4(3H)-one;
3-cyclooctyl-7-(2-fluorophenyl)thieno[3,2-d]pyrimidin-4(3H)-one;
3-(cyclopropylmethyl)-7-(2-fluorophenyl)thieno[3,2-d]pyrimidin-4(3H)-one;
3-(cyclohexanemethyl)-7-(2-fluorophenyl)thieno[3,2-d]pyrimidin-4(3H)-one;
7-(2-fluorophenyl)-3-((1R,4R)-4-methylcyclohexyl)thieno[3,2-d]pyrimidin -4(3H)-one;
3-cycloheptyl-7-phenylthieno[3,2-d]pyrimidin-4(3H)-one;
3-cycloheptyl-7-(2-fluorophenyl)thieno[3,2-d]pyrimidin-4(3H)-one;
3-(2,3-dihydro-1H-inden-2-yl)-7-phenylthieno[3,2-d]pyrimidin-4(3H)-one;
3-(4-isopropylcyclohexyl)-7-phenylthieno[3,2-d]pyrimidin-4(3H)-one;
7-phenyl-3-(4-propylcyclohexyl)thieno[3,2-d]pyrimidin-4(3H)-one;
3-(4-(tert-butyl)cyclohexyl)-7-phenylthieno[3,2-d]pyrimidin-4(3H)-one;
(1r,4r)-4-(7-(2-fluorophenyl)-4-oxothieno[3,2-d]pyrimidin-3(4H)-yl)cyclohexyl acetate;
7-(2-fluorophenyl)-3-isobutylthieno[3,2-d]pyrimidin-4(3H)-one;
7-(2-fluorophenyl)-3-neopentylthieno[3,2-d]pyrimidin-4(3H)-one;
3-cyclooctyl-7-(o-tolyl)thieno[3,2-d]pyrimidin-4(3H)-one; and
3-cycloheptyl-7-(o-tolyl)thieno[3,2-d]pyrimidin-4(3H)-one.

In another aspect, the present invention provides a pharmaceutical composition for treating a brain disease, including at least one of the thienopyrimidinone derivatives according to the embodiments of the present invention or a pharmaceutically acceptable salt thereof as an active ingredient.

In one embodiment, the brain disease is selected from pain, a psychiatric disease, urinary incontinence, Parkinson's disease, and Alzheimer's disease.

In a further embodiment, the pain is neuropathic pain or migraine, and the psychiatric disease is anxiety disorder or schizophrenia.

The pharmaceutical composition of the present invention may be formulated into a dosage form suitable for oral or parenteral administration by compounding the thienopyrimidinone compound of Formula 1 or 2 or pharmaceutically acceptable salt thereof with one or more suitable additives selected from carriers, auxiliaries and diluents. The formulation may be carried out by a suitable technique known in the art. For oral administration, the pharmaceutical composition of the present invention may be in the form of tablets, capsules, solutions, syrups, etc. For parenteral administration, the pharmaceutical composition of the present invention may be in the form of intraperitoneal, subcutaneous, intramuscular, transdermal injectables, etc.

The daily effective dose of the pharmaceutical composition according to the present invention as an mGluR1 modulator is in the range of 0.01 to 1000 mg/day for an adult patient depending on the age, body weight, sex, mode of administration, general health, and severity of disease. The daily dose of the pharmaceutical composition may be administered in a single dose or in divided doses at regular time intervals according to the judgment of the physician or pharmacist.

In another aspect, the present invention provides a method for preparing the thienopyrimidinone derivative of Formula 1 or 2.

Specifically, the method of the present invention includes (a) formylating an aryl acetonitrile 2 to afford an aryl hydroxyacrylonitrile 3, (b) methylating the compound 3 to afford an aryl methoxyacrylonitrile 4, (c) forming a thiophene ring from the aryl methoxyacrylonitrile to synthesize a thiophene derivative 5, and (d) synthesizing the thienopyrimidinone derivative 1 from the thiophene derivative, as depicted in Reaction Scheme 1:

Reaction Scheme 1

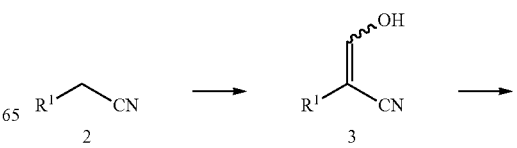

-continued

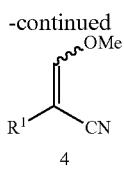

4

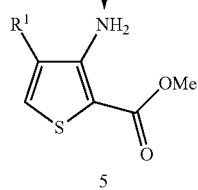

5

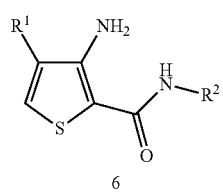

6

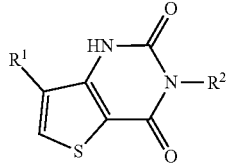

7

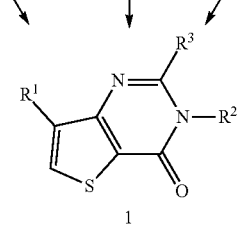

1

In one embodiment, in step (d), (i) the thienopyrimidinone derivative 1 is directly synthesized from the thiophene derivative, (ii) the thiophene derivative is amidated to synthesize a compound 6 and a pyrimidinone ring is formed to synthesize the thienopyrimidinone derivative 1, or (iii) the thiophene derivative is reacted with an isocyanate to synthesize a thienopyrimidinedione derivative 7 and an amine is introduced to prepare the thienopyrimidinone derivative 1.

Specifically, the aryl acetonitrile 2 is formylated to afford the aryl hydroxyacrylonitrile 3. The formylation may be carried out using a base. Examples of suitable bases include NaH and $NaN(SiMe_3)_2$. The formyl group may be introduced using an alkyl formate. Examples of suitable alkyl formates include ethyl formate and methyl formate. General organic solvents may be used in the formylation, and specific examples thereof include tetrahydrofuran, dioxane, N,N-dimethylformamide, acetonitrile, and dichloromethane. The formylation is preferably carried out at a temperature of −20° C. to 80° C. for 1 to 24 hours.

The aryl hydroxyacrylonitrile 3 is methylated to afford the aryl methoxyacrylonitrile 4. The methylation may be carried out using a base. Examples of suitable bases include NaH and $NaN(SiMe_3)_2$. The methyl group may be introduced using various methylation reagents, such as methyl iodide and dimethyl sulfate. General organic solvents may be used in the methylation, and specific examples thereof include tetrahydrofuran, dioxane, N,N-dimethylformamide, acetonitrile, and dichloromethane. The methylation is preferably carried out at a temperature of 0° C. to 100° C. for 1 to 24 hours.

The thiophene derivative 5 including a thiophene ring is synthesized from the aryl methoxyacrylonitrile 4. The thiophene derivative 5 may be synthesized using various bases, such as NaOMe, MaOEt and KOtOBu. Specifically, the aryl methoxyacrylonitrile 4 is reacted with an alkyl thioglycolate, such as methyl thioglycolate, at 50 to 150° C. with stirring for 12 to 36 hours. After completion of the reaction, the reaction mixture is extracted with an organic solvent and purified by column chromatography to obtain the thiophene compound 5. General organic solvents may be used in the reaction, and specific examples thereof include methanol, ethanol, tetrahydrofuran, dioxane, N,N-dimethylformamide, acetonitrile, and dichloromethane.

The target compound 1 can be prepared from the thiophene compound 5 by the following three methods. According to the first method, the compound 5 is mixed with a triethyl orthocarboxylate, such as triethyl orthoformate or triethyl orthoacetate, an amine, and acetic acid, and the mixture is heated with stirring to obtain the thienopyrimidinone compound 1. The reaction is desirably carried out at about 1 to about 5 atm and a temperature of 50 to 200° C. for 12 to 36 hours.

According to the second method, the compound 5 is amidated to synthesize the compound 6 and a pyrimidinone ring is formed to synthesize the thienopyrimidinone derivative 1. The amide compound 6 is prepared by reacting the thiophene compound 5 with an amine in the presence of a Lewis acid, such as trimethylaluminum. Starting from −20 to 15° C., the reaction temperature is raised with stirring. The compound 6 is then mixed with a triethyl orthocarboxylate, such as triethyl orthoformate or triethyl orthoacetate, and acetic acid. The mixture is heated with stirring to afford the thienopyrimidinone compound 1. According to the third method, the thiophene compound 5 is reacted with an isocyanate to prepare the thienopyrimidinedione 7, which is then aminated by a suitable method known in the art to synthesize the thienopyrimidinone compound 1 having R3 including the amine.

Specifically, the thienopyrimidinone compound 7 is chlorinated with N,N-diethylaniline and phosphoryl chloride (phosphorus oxychloride) by a method known in the art to obtain an intermediate. The intermediate is reacted with an amine in the presence of a base to obtain the thienopyrimidinone compound 1 as the target compound. The amine is included in the thienopyrimidinone compound 1.

In yet another aspect, the present invention provides a method for treating or preventing a brain disease. Specifically, the method includes administering to a mammal in need of such treatment at least one of the target compounds according to the embodiments of the present invention or the pharmaceutical composition including at least one of the target compounds.

That is, the present invention provides the medical use of the thienopyrimidinone compound of Formula 1 or pharmaceutically acceptable salt thereof or the pharmaceutical composition for the prevention and treatment of diseases.

Specifically, the present invention includes the medical use of the thienopyrimidinone compound as an mGluR1 modulator for the prevention and treatment of pain, such as neuropathic pain and migraine, psychiatric diseases, such as anxiety disorder and schizophrenia, urinary incontinence, and neurodegenerative diseases, such as Parkinson's disease and Alzheimer's disease.

The pharmaceutically acceptable salt of the thienopyrimidinone derivative of Formula 1 or 2 according to the present invention may be formed by any suitable method known in the art. For example, suitable pharmaceutically acceptable acid addition salts may also be formed through the addition of a non-toxic inorganic acid or organic acid. Examples of suitable non-toxic inorganic acids include hydrochloric acid, hydrobromic acid, sulfonic acid, amidosulfuric acid, phosphoric acid, and nitric acid. Examples of suitable non-toxic organic acids include acetic acid, propionic acid, succinic acid, glycolic acid, stearic acid, lactic acid, tartaric acid, citric acid, para-toluenesulfonic acid, and methanesulfonic acid.

A more detailed explanation of the substituents used to define the thienopyrimidinone derivative of Formula 1 or 2 according to the present invention will be provided below.

The term "aryl" is intended to include phenyl, substituted phenyl, naphthyl, and benzodioxazole groups. The term "alkyl" is intended to include straight, branched and cyclic carbon chains having 1 to 12 carbon atoms. Preferred alkyl groups are, for example, methyl, ethyl, n-propyl, isopropyl, allyl, n-butyl, isobutyl, tert-butyl, neopentyl, cyclobutyl, cyclopentyl, cyclohexyl, cycloheptyl, cyclooctyl, cyclopropylmethyl, cyclohexylmethyl, methylcyclohexyl, ethylcyclohexyl, propylcyclohexyl, isopropylcyclohexyl, tert-butylcyclohexyl, tetrahydronaphthyl, heteroalkyl (e.g., tetrahydrofurfuryl and N-methylpiperidinyl), hydroxycyclohexyl, oxocyclohexyl, and tetrahydropyranyl groups. The term "alkoxy" refers to an alkyl group attached to oxygen wherein the alkyl is as defined above.

The present invention will be explained in more detail with reference to the following examples, including formulation examples and experimental example. However, these examples are not to be construed as limiting or restricting the scope and spirit of the invention. It is to be understood that based on the teachings of the present invention including the following examples, those skilled in the art can readily practice other embodiments of the present invention whose specific experimental data are not available.

Although there are differences in the structures and physical properties of the substituents depending on the kind of the substituents, the reaction principles and conditions of the Examples Section can also be applied to compounds including substituents that are not described in the Examples Section. Therefore, it is obvious that those skilled in the art can easily prepare the compounds including substituents based on the disclosure of the Examples Section and the common knowledge in the art.

EXAMPLES

Example 1

3-Hydroxy-2-phenylacrylonitrile

Phenylacetonitrile (10 g, 85.4 mmol) and methyl formate (67 ml) were dissolved in THF (250 ml) in a reaction vessel, and then NaH (2.6 g, 106.7 mmol) was added thereto at 0° C. The solution was stirred at room temperature for 12 hr. After completion of the reaction, the reaction mixture was washed with distilled water and acidified with 1 N HCl to adjust the pH to 5 or less. Thereafter, the resulting solution was extracted with dichloromethane. The organic layer was dried over anhydrous $Na_2SO_4$, followed by filtration. The filtrate was concentrated under reduced pressure to give 12.3 g (84.7 mmol, quant.) of the title compound.

$^1$H NMR (300 MHz, $CDCl_3$) δ 7.44-7.32 (m, 5H)

Example 2

3-Methoxy-2-phenylacrylonitrile

3-Hydroxy-2-phenylacrylonitrile (12.3 g, 84.7 mmol) was dissolved in dry THF (100 ml) in a reaction vessel, and then NaH (4.1 g, 169.4 mmol) was slowly added thereto. The mixture was stirred at room temperature for 2 hr. Thereafter, dimethyl sulfate (13.7 ml, 144.0 mmol) was added, followed by stirring at 40° C. for 12 hr. After completion of the reaction, the reaction mixture was washed with distilled water and concentrated under reduced pressure. The concentrate was diluted with EtOAc and extracted with EtOAc together with distilled water. The organic layer was dried over anhydrous $MgSO_4$ and filtered. The filtrate was concentrated under reduced pressure to give 17.9 g (112.5 mmol, quant.) of the title compound.

$^1$H NMR (300 MHz, $CDCl_3$) δ 7.40-7.28 (m, 5H), 4.00 (s, 3H)

Example 3

Methyl 3-amino-4-phenylthiophene-2-carboxylate

3-Methoxy-2-phenylacrylonitrile (17.9 g, 112.5 mmol) was dissolved in NaOMe (5 M in MeOH, 31.5 ml, 157.5 mmol), and then methyl thioglycolate (16 ml, 180.0 mmol) was added thereto. The mixture was heated with stirring at 65° C. for 24 hr. After the completion of the reaction was confirmed by thin layer chromatography (TLC), the reaction mixture was cooled to room temperature and filtered through Celite. The filtrate was washed with distilled water and extracted with dichloromethane. The organic layer was dried over anhydrous $MgSO_4$ and filtered. The filtrate was distilled under reduced pressure, and the concentrate was purified by silica gel column chromatography (EtOAc:Hex=1:5) to give 5.1 g (21.9 mmol, 26% yield in three steps) of the title compound.

$^1$H NMR (300 MHz, $CDCl_3$) δ 7.49-7.39 (m, 5H), 7.25 (s, 1H), 5.64 (br, 2H), 3.88 (s, 3H)

Example 4

3-Amino-N-(4-methoxyphenyl)-4-phenylthiophene-2-carboxamide p-Anisidine (29 mg, 0.24 mmol) was dissolved in toluene (2 ml) in a reaction vessel, and trimethylaluminum (2 M in THF, 0.12 ml) was added thereto at 0° C. After stirring for 10 min, to the mixture was added methyl 3-amino-4-phenylthiophene-2-carboxylate (50 mg, 0.21 mmol). The resulting mixture was heated to reflux at 120° C. for 16 hr. The completion of the reaction was confirmed by TLC. The reaction mixture was allowed to cool to room temperature, extracted with EtOAc, dried over anhydrous $MgSO_4$, and concentrated under reduced pressure. The concentrate was purified by silica gel column chromatography (hexane:EtOAc=5:1) to give (57 mg, 0.18 mmol, 84% yield) of the title compound.

$^1$H NMR (300 MHz, $CDCl_3$) δ 7.47-7.37 (m, 7H), 7.16 (s, 1H), 7.07 (brs, 1H), 6.93-6.89 (m, 2H), 5.86 (brs, 2H), 3.81 (s, 3H)

Compound 1:
3,7-Diphenylthieno[3,2-d]pyrimidin-4(3H)-one

Methyl 3-amino-4-phenylthiophene-2-carboxylate (100 mg, 0.43 mmol), triethyl orthoformate (1 ml), aniline (76 mg, 0.81 mmol), and acetic acid (0.1 ml) were placed in a pressure bottle. The mixture was heated with stirring at 160° C. for 18 hr. After the completion of the reaction was confirmed by TLC, the reaction mixture was cooled to room temperature and solidified with diethyl ether and EtOAc to give 42 mg (0.14 mmol, 33% yield) of the title compound as a final product.

$^1$H NMR (400 MHz, CDCl$_3$) δ 8.53 (s, 1H), 8.51 (s, 1H), 8.01 (d, J=7.2 Hz, 2H), 7.63-7.55 (m, 5H), 7.52 (t, J=7.6 Hz, 2H), 7.42 (t, J=7.4 Hz, 1H)

Compound 2: 3-(2-Fluorophenyl)-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), 2-fluoroaniline (88.6 mg, 0.8 mmol), and acetic acid (0.12 ml) were used to give 36 mg (0.11 mmol, 26% yield) of the title compound.

$^1$H NMR (400 MHz, CDCl$_3$) δ 8.12 (s, 1H), 7.91 (s, 1H), 7.84 (d, J=1.4 Hz, 2H), 7.53-7.30 (m, 7H)

Compound 3: 3-(3-Fluorophenyl)-7-phenylthieno[3,2-d]pyrimidin-4(3H)-one

In the same manner as the synthesis of Compound 1, methyl 3-amino-4-phenylthiophene-2-carboxylate (50 mg, 0.21 mmol), triethyl orthoformate (0.47 ml), 3-fluoroaniline (44.3 mg, 0.4 mmol), and acetic acid (0.06 ml) were used to give 8.1 mg (0.025 mmol, 12% yield) of the title compound.

$^1$H NMR (300 MHz, CDCl$_3$) δ 8.17 (s, 1H), 7.91 (s, 1H), 7.85-7.82 (m, 2H), 7.60-7.38 (m, 5H), 7.42-7.21 (m, 2H)

Compound 4: 3-(4-Fluorophenyl)-7-phenylthieno[3,2-d]pyrimidin-4(3H)-one

In the same manner as the synthesis of Compound 1, methyl 3-amino-4-phenylthiophene-2-carboxylate (76 mg, 0.33 mmol), triethyl orthoformate (0.66 ml), 4-fluoroaniline (0.058 mg, 0.61 mmol), and acetic acid (0.08 ml) were used to give 68.5 mg (0.021 mmol, 64% yield) of the title compound.

$^1$H NMR (300 MHz, CDCl$_3$) δ 8.18 (s, 1H), 7.92 (s, 1H), 7.90-7.83 (m, 2H), 7.54-7.40 (m, 5H), 7.31-7.24 (m, 2H)

Compound 5: 3-(2-Chlorophenyl)-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), 2-chlorophenyl (102.1 mg, 0.8 mmol), and acetic acid (0.06 ml) were used to give 19.2 mg (0.057 mmol, 13.2% yield) of the title compound.

$^1$H NMR (300 MHz, CDCl$_3$) δ 8.04 (s, 1H), 7.91 (s, 1H), 7.87-7.83 (m, 2H), 7.64-7.62 (m, 1H), 7.53-7.41 (m, 6H)

Compound 6: 3-(3-Chlorophenyl)-7-phenylthieno[3,2-d]pyrimidin-4(3H)-one

In the same manner as the synthesis of Compound 1, methyl 3-amino-4-phenylthiophene-2-carboxylate (50 mg, 0.21 mmol), triethyl orthoformate (0.47 ml), 3-chlorophenyl (50.9 mg, 0.21 mmol), and acetic acid (0.06 ml) were used to give 16 mg (0.047 mmol, 22.5% yield) of the title compound.

$^1$H NMR (300 MHz, CDCl$_3$) δ 8.13 (s, 1H), 7.89 (s, 1H), 7.85-7.81 (m, 2H), 7.54-7.45 (m, 5H), 7.42-7.30 (m, 2H)

Compound 7: 3-(4-Chlorophenyl)-7-phenylthieno[3,2-d]pyrimidin-4(3H)-one

In the same manner as the synthesis of Compound 1, methyl 3-amino-4-phenylthiophene-2-carboxylate (60 mg, 0.26 mmol), triethyl orthoformate (0.5 ml), 4-chloroaniline (61 mg, 0.48 mmol), and acetic acid (0.06 ml) were used to give 31.6 mg (0.093 mmol, 36% yield) of the title compound.

$^1$H NMR (300 MHz, CDCl$_3$) δ 8.19 (s, 1H), 7.93 (s, 1H), 7.86 (d, J=1.4 Hz, 2H), 7.58-7.50 (m, 4H), 7.46-7.40 (m, 3H)

Compound 8: 3-(3-Bromophenyl)-7-phenylthieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), 3-bromoaniline (280 mg, 1.63 mmol), and acetic acid (0.2 ml) were used to give 40 mg (0.10 mmol, 12%) yield) of the title compound.

$^1$H NMR (400 MHz, CDCl$_3$) δ 8.19 (s, 1H), 7.94 (s, 1H), 7.88-7.86 (m, 2H), 7.70-7.68 (m, 2H), 7.56-7.42 (m, 5H)

Compound 9: 3-(4-Bromophenyl)-7-phenylthieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), 4-bromoaniline (280 mg, 1.63 mmol), and acetic acid (0.2 ml) were used to give 13 mg (0.034 mmol, 4% yield) of the title compound.

$^1$H NMR (400 MHz, CDCl$_3$) δ 7.18 (s, 1H), 7.93 (s, 1H), 7.87-7.85 (m, 2H), 7.74-7.70 (m, 2H), 7.55-7.51 (m, 2H), 7.46-7.42 (m, 1H), 7.38-7.35 (m, 2H)

Compound 10: 3-(2-Methoxyphenyl)-7-phenylthieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), o-anisidine (201 mg, 1.63 mmol), and acetic acid (0.2 ml) were used to give 204 mg (0.61 mmol, 71% yield) of the title compound.

$^1$H NMR (400 MHz, CDCl$_3$) δ 8.09 (s, 1H), 7.91-7.88 (m, 3H), 7.54-7.38 (m, 5H), 7.14 (t, J=8.2 Hz, 2H), 3.85 (s, 3H)

Compound 11: 3-(3-Methoxyphenyl)-7-phenylthieno[3,2-d]pyrimidin-4(3H)-one

In the same manner as the synthesis of Compound 1, methyl 3-amino-4-phenylthiophene-2-carboxylate (70 mg, 0.30 mmol), triethyl orthoformate (0.57 ml), m-anisidine (0.063 ml, 0.56 mmol), and acetic acid (0.07 ml) were used to give 83 mg (0.25 mmol, 83% yield) of the title compound.

$^1$H NMR (300 MHz, CDCl$_3$) δ 8.22 (s, 1H), 7.93-7.81 (m, 3H), 7.55-7.41 (m, 4H), 7.12-7.04 (m, 3H), 3.88 (s, 3H)

Compound 12: 3-(4-Methoxyphenyl)-7-phenylthieno[3,2-d]pyrimidin-4(3H)-one

In the same manner as the synthesis of Compound 1, methyl 3-amino-4-phenylthiophene-2-carboxylate (58 mg, 0.25 mmol), triethyl orthoformate (0.5 ml), p-anisidine (58 mg, 0.47 mmol), and acetic acid (0.06 ml) were used to give 26 mg (0.078 mmol, 31% yield) of the title compound.

$^1$H NMR (300 MHz, CDCl$_3$) δ 8.20 (s, 1H), 7.90-7.85 (m, 3H), 7.54-7.45 (m, 2H), 7.45-7.36 (m, 3H), 7.06 (d, J=6.8 Hz, 2H), 3.89 (s, 3H)

Compound 13: 3-(3,4-Dimethoxyphenyl)-7-phenylthieno[3,2-d]pyrimidin-4(3H)-one

In the same manner as the synthesis of Compound 1, methyl 3-amino-4-phenylthiophene-2-carboxylate (52 mg, 0.22 mmol), triethyl orthoformate (0.45 ml), 3,4-dimethoxyaniline (62.8 mg, 0.41 mmol), and acetic acid (0.06 ml) were used to give 48 mg (0.13 mmol, 59% yield) of the title compound.

$^1$H NMR (300 MHz, CDCl$_3$) δ 8.22 (s, 1H), 7.90-7.86 (m, 3H), 7.54-7.40 (m, 3H), 7.03-6.94 (m, 3H), 3.97 (s, 3H), 3.93 (s, 3H)

Compound 14: 3-(3,5-Dimethoxyphenyl)-7-phenylthieno[3,2-d]pyrimidin-4(3H)-one

In the same manner as the synthesis of Compound 1, methyl 3-amino-4-phenylthiophene-2-carboxylate (72.3 mg, 0.31 mmol), triethyl orthoformate (0.62 ml), 3,5-dimethoxyaniline (88.8 mg, 0.58 mmol), and acetic acid (0.07 ml) were used to give 75.7 mg (0.21 mmol, 68% yield) of the title compound.

$^1$H NMR (300 MHz, CDCl$_3$) δ 8.24 (s, 1H), 7.91-7.86 (m, 3H), 7.55-7.41 (m, 3H), 6.61 (s, 3H), 3.85 (s, 6H)

Compound 15: 3-(4-Hydroxyphenyl)-7-phenylthieno[3,2-d]pyrimidin-4(3H)-one

In the same manner as the synthesis of Compound 1, methyl 3-amino-4-phenylthiophene-2-carboxylate (500 mg, 2.14 mmol), triethyl orthoformate (5 ml), 4-aminophenol (444 mg, 4.07 mmol), and acetic acid (0.5 ml) were used to give 283 mg (0.88 mmol, 41% yield) of the title compound.

$^1$H NMR (300 MHz, DMSO) δ 9.89 (brs, 1H), 8.47 (s, 1H), 8.44 (s, 1H), 7.98 (d, J=7.2 Hz, 2H), 7.52-7.32 (m, 5H), 6.94-6.89 (m, 2H)]

Compound 16: 7-Phenyl-3-(o-tolyl)thieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), o-toluidine (175 mg, 1.63 mmol), and acetic acid (0.2 ml) were used to give 62 mg (0.19 mmol, 23% yield) of the title compound.

$^1$H NMR (400 MHz, CDCl$_3$) δ 8.11 (s, 1H), 7.94 (s, 1H), 7.91-7.89 (m, 2H), 7.55-7.39 (m, 6H), 7.30 (d, J=7.6 Hz, 1H), 2.26 (s, 3H)

Compound 17: 7-Phenyl-3-(m-tolyl)thieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), m-toluidine (175 mg, 1.63 mmol), and acetic acid (0.2 ml) were used to give 40 mg (0.13 mmol, 15% yield) of the title compound.

$^1$H NMR (400 MHz, CDCl$_3$) δ 8.21 (s, 1H), 7.91 (s, 1H), 7.88 (d, J=7.6 Hz, 2H), 7.54-7.25 (m, 7H), 2.48 (s, 3H)

Compound 18: 7-Phenyl-3-p-tolylthieno[3,2-d]pyrimidin-4(3H)-one

In the same manner as the synthesis of Compound 1, methyl 3-amino-4-phenylthiophene-2-carboxylate (80 mg, 0.34 mmol), triethyl orthoformate (0.65 ml), p-toluidine (67.5 mg, 0.63 mmol), and acetic acid (0.08 ml) were used to give 73.8 mg (0.23 mmol, 68% yield) of the title compound.

$^1$H NMR (300 MHz, CDCl$_3$) δ 8.21 (s, 1H), 7.91-7.88 (m, 3H), 7.55-7.34 (m, 7H), 2.48 (s, 3H)

Compound 19: 3-(4-Ethylphenyl)-7-phenylthieno[3,2-d]pyrimidin-4(3H)-one

In the same manner as the synthesis of Compound 1, methyl 3-amino-4-phenylthiophene-2-carboxylate (50 mg, 0.21 mmol), triethyl orthoformate (0.42 ml), 4-ethylaniline (0.05 ml, 0.39 mmol), and acetic acid (0.05 ml) were used to give 59.5 mg (0.18 mmol, 60% yield) of the title compound.

$^1$H NMR (300 MHz, CDCl$_3$) δ 8.23 (s, 1H), 7.92-7.87 (m, 3H), 7.55-7.37 (m, 7H), 2.78 (q, J=7.8 Hz, 2H), 1.34 (t, J=7.8 Hz, 3H)

Compound 20: 3-(2,6-Dimethylphenyl)-7-phenylthieno[3,2-d]pyrimidin-4(3H)-one

In the same manner as the synthesis of Compound 1, methyl 3-amino-4-phenylthiophene-2-carboxylate (43 mg, 0.18 mmol), triethyl orthoformate (0.34 ml), 2,6-dimethylaniline (0.04 ml, 0.33 mmol), and acetic acid (0.042 ml) were used to give 34.8 mg (0.10 mmol, 56% yield) of the title compound.

$^1$H NMR (300 MHz, CDCl$_3$) δ 8.00 (s, 1H), 7.96 (s, 1H), 7.94-7.90 (m, 2H), 7.58-7.19 (m, 6H), 2.20 (s, 6H)

Compound 21: 3-(2,5-Dimethylphenyl)-7-phenylthieno[3,2-d]pyrimidin-4(3H)-one

In the same manner as the synthesis of Compound 1, methyl 3-amino-4-phenylthiophene-2-carboxylate (45.6 mg, 0.20 mmol), triethyl orthoformate (0.40 ml), 2,5-dimethylaniline (44.8 mg, 0.37 mmol), and acetic acid (0.05 ml) were used to give 28.8 mg (0.087 mmol, 44% yield) of the title compound.

$^1$H NMR (300 MHz, CDCl$_3$) δ 8.11 (s, 1H), 7.95-7.87 (m, 3H), 7.57-7.26 (m, 5H), 7.12 (s, 1H), 2.34 (s, 3H), 2.21 (s, 3H)

Compound 22: 3-(3,4-Dimethylphenyl)-7-phenylthieno[3,2-d]pyrimidin-4(3H)-one

In the same manner as the synthesis of Compound 1, methyl 3-amino-4-phenylthiophene-2-carboxylate (70 mg, 0.30 mmol), triethyl orthoformate (0.57 ml), 3,4-dimethylaniline (67.8 mg, 0.56 mmol), and acetic acid (0.07 ml) were used to give 49.2 mg (0.15 mmol, 50% yield) of the title compound.

$^1$H NMR (300 MHz, CDCl$_3$) δ 8.21 (s, 1H), 7.92-7.88 (m, 3H), 7.56-7.18 (m, 6H), 2.38 (s, 6H)

Compound 23: 3-(4-Oxo-7-phenylthieno[3,2-d]pyrimidin-3(4H)-yl)benzonitrile

In the same manner as the synthesis of Compound 1, methyl 3-amino-4-phenylthiophene-2-carboxylate (100 mg, 0.43 mmol), triethyl orthoformate (1 ml), 3-aminobenzonitrile (96 mg, 0.81 mmol), and acetic acid (0.1 ml) were used to give 20 mg (0.061 mmol, 14% yield) of the title compound.

$^1$H NMR (400 MHz, CDCl$_3$) δ 8.58 (s, 1H), 8.54 (s, 1H), 8.19 (t, J=1.6 Hz, 1H), 8.05 (d, J=6.0 Hz, 1H), 8.00 (d, J=7.2 Hz, 3H), 7.82 (t, J=8.0 Hz, 1H), 7.52 (t, J=7.6 Hz, 2H), 7.43 (t, J=7.4 Hz, 1H)

Compound 24: 4-(4-Oxo-7-phenylthieno[3,2-d]pyrimidin-3(4H)-yl)benzonitrile

In the same manner as the synthesis of Compound 1, methyl 3-amino-4-phenylthiophene-2-carboxylate (100 mg, 0.43 mmol), triethyl orthoformate (1 ml), 4-aminobenzonitrile (96 mg, 0.81 mmol), and acetic acid (0.1 ml) were used to give 38 mg (0.12 mmol, 27% yield) of the title compound.
$^1$H NMR (400 MHz, CDCl$_3$) δ 8.56 (s, 1H), 8.53 (s, 1H), 8.11 (d, J=7.6 Hz, 2H), 7.99 (d, J=8.0 Hz, 2H), 7.85 (d, J=7.6 Hz, 2H), 7.52 (t, J=8.4 Hz, 2H), 7.45-7.41 (m, 1H)

Compound 25: 7-Phenyl-3-(3-trifluoromethyl)phenyl)thieno[3,2-d]pyrimidin-4(3H)-one In the same manner as the synthesis of Compound 1, methyl 3-amino-4-phenylthiophene-2-carboxylate (200 mg, 0.86 mmol), triethyl orthoformate (2 ml), 3-trifluoromethylaniline (263 mg, 1.63 mmol), and acetic acid (0.2 ml) were used to give 12 mg (0.032 mmol, 4% yield) of the title compound.
$^1$H NMR (400 MHz, CDCl$_3$) δ 8.21 (s, 1H), 7.95 (s, 1H), 7.87 (d, J=6.8 Hz, 2H), 7.83-7.69 (m, 4H), 7.53 (t, J=7.4 Hz, 2H), 7.45 (t, J=7.4 Hz, 1H)

Compound 26: 7-Phenyl-3-(4-(trifluoromethyl)phenyl)thieno[3,2-d]pyrimidin-4(3H)-one In the same manner as the synthesis of Compound 1, methyl 3-amino-4-phenylthiophene-2-carboxylate (50 mg, 0.21 mmol), triethyl orthoformate (0.40 ml), p-trifluoromethaneaniline (0.05 ml, 0.39 mmol), and acetic acid (0.06 ml) were used to give 12.2 mg (0.033 mmol, 16% yield) of the title compound.
$^1$H NMR (300 MHz, CDCl$_3$) δ 8.22 (s, 1H), 7.97 (s, 1H), 7.90-7.86 (m, 4H), 7.65 (d, J=8.4 Hz, 2H), 7.54 (t, J=7.8 Hz, 2H), 7.48-7.30 (m, 1H)

Compound 27: 7-Phenyl-3-(4-trifluoro methoxy) phenyl)thieno[3,2-d]pyrimidin-4(3H)-one In the same manner as the synthesis of Compound 1, methyl 3-amino-4-phenylthiophene-2-carboxylate (200 mg, 0.86 mmol), triethyl orthoformate (2 ml), 4-trifluoromethoxyaniline (289 mg, 1.63 mmol), and acetic acid (0.2 ml) were used to give 70 mg (0.18 mmol, 21% yield) of the title compound.
$^1$H NMR (400 MHz, CDCl$_3$) δ 8.27 (s, 1H), 7.92 (s, 1H), 7.87-7.85 (m, 2H), 7.54-7.50 (m, 4H), 7.46-7.42 (m, 3H)

Compound 28: 3-(4-Nitrophenyl)-7-phenylthieno[3,2-d]pyrimidin-4(3H)-one

In the same manner as the synthesis of Compound 1, methyl 3-amino-4-phenylthiophene-2-carboxylate (200 mg, 0.86 mmol), triethyl orthoformate (2 ml), 4-nitroaniline (225 mg, 1.63 mmol), and acetic acid (0.2 ml) were used to give 31 mg (0.089 mmol, 10% yield) of the title compound.
$^1$H NMR (400 MHz, CDCl$_3$) δ 8.46 (d, J=8.8 Hz, 1H), 8.22 (s, 1H), 7.97 (s, 1H), 7.86 (d, J=7.6 Hz, 2H), 7.72 (d, J=8.4 Hz, 2H), 7.54 (t, J=7.4 Hz, 2H), 7.47-7.45 (m, 1H)

Compound 29: 7-Phenyl-3-(3-vinylphenyl)thieno[3, 2-d]-pyrimidin-4(3H)-one

In the same manner as the synthesis of Compound 1, methyl 3-amino-4-phenylthiophene-2-carboxylate (50 mg, 0.21 mmol), triethyl orthoformate (0.47 ml), 4-vinylaniline (47.5 mg, 0.39 mmol), and acetic acid (0.06 ml) were used to give 8 mg (0.024 mmol, 11.5% yield) of the title compound.
$^1$H NMR (300 MHz, CDCl$_3$) δ 8.22 (s, 1H), 7.9 (s, 1H), 7.86-7.83 (m, 2H), 7.61-7.48 (m, 5H), 7.44-7.38 (m, 1H), 7.36-7.31 (m, 1H), 6.76 (dd, J=23.6, 14.4 Hz, 1H), 5.82 (d, J=23.6 Hz, 1H), 5.37 (d, J=14.4 Hz, 1H)

Compound 30: 7-Phenyl-3-(4-vinylphenyl)thieno[3, 2-d]pyrimidin-4(3H)-one

In the same manner as the synthesis of Compound 1, methyl 3-amino-4-phenylthiophene-2-carboxylate (100 mg, 0.43 mmol), triethyl orthoformate (1 ml), 4-aminostyrene (97 mg, 0.81 mmol), and acetic acid (0.1 ml) were used to give 10 mg (0.030 mmol, 7% yield) of the title compound.
$^1$H NMR (400 MHz, CDCl$_3$) δ 8.53 (s, 1H), 8.52 (s, 1H), 8.01 (d, J=8.4 Hz, 2H), 7.69 (d, J=8.4 Hz, 2H), 7.58-7.40 (m, 5H), 6.89-6.82 (m, 1H), 5.98 (d, J=17.6 Hz, 1H), 5.40 (d, J=10.8 Hz, 1H)

Compound 31: 3-(4-Fluorophenyl)-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (88 mg, 0.35 mmol), triethyl orthoformate (0.77 ml), 4-fluoroaniline (63 ml, 0.46 mmol), and acetic acid (0.09 ml) were used to give 32 mg (0.095 mmol, 27% yield) of the title compound.
$^1$H NMR (300 MHz, CDCl$_3$) δ 8.2 (s, 1H), 8.07 (d, J=1.5 Hz, 1H), 7.6 (td, J=7.6, 1.7 Hz, 1H), 7.49-7.40 (m, 3H), 7.35-7.23 (m, 4H)

Compound 32: 3-(4-Chlorophenyl)-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 40 mmol), triethyl orthoformate (2.0 ml), 4-chloroaniline (94.43 mg, 0.74 mmol), and acetic acid (0.1 ml) were used to give 38 mg (0.11 mmol, 27% yield) of the title compound.
$^1$H NMR (300 MHz, CDCl$_3$) δ 8.15 (s, 1H), 8.03 (s, 1H), 7.85-7.84 (m, 1H), 7.58 (d, J=8.4 Hz, 2H), 7.44 (d, J=11.4 Hz, 2H), 7.40-7.26 (m, 3H)

Compound 33: 7-(2-Fluorophenyl)-3-(4-methoxyphenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (2.0 ml), p-anisidine (91.17 mg, 0.74 mmol), and acetic acid (0.1 ml) were used to give 22 mg (0.062 mmol, 16% yield) of the title compound.
$^1$H NMR (300 MHz, CDCl$_3$) δ 8.20 (s, 1H), 8.05 (s, 1H), 8.04-7.89 (m, 1H), 7.40-7.28 (m, 5H), 7.10-7.07 (m, 2H), 3.91 (s, 3H)

Compound 34: 7-(2-Fluorophenyl)-3-(4-hydroxyphenyl)thieno[3,2-d]pyrimidin-4(3H)-one In the same manner as the synthesis of Compound 1, methyl 3-amino-4-(2-fluorophenyl)thiophene-2-carboxylate (500 mg, 1.99 mmol), triethyl orthoformate (5 ml), 4-aminophenol (412 mg, 3.78 mmol), and acetic acid (0.5 ml) were used to give 328 mg (0.97 mmol, 49% yield) of the title compound.
$^1$H NMR (300 MHz, DMSO) δ 9.90 (s, 1H), 8.40 (s, 1H), 7.81 (td, J=7.7 Hz, J=1.5 Hz, 1H), 7.52-7.44 (m, 1H), 7.38-7.30 (m, 4H), 6.93-6.90 (m, 1H)

Compound 35: 7-(2-Fluorophenyl)-3-(3-hydroxyphenyl)thieno[3,2-d]pyrimidin-4(3H)-one In the same manner as the synthesis of Compound 1, methyl 3-amino-4-(2-fluorophenyl)thiophene-2-carboxylate (80 mg, 0.3 mmol), triethyl orthoformate (0.72 ml), 3-aminophenol (64.6 mg, 0.59 mmol), and acetic acid (0.09 ml) were used to give 41.5 mg (0.12 mmol, 38.3% yield) of the title compound.

$^1$H NMR (300 MHz, DMSO) δ 9.96 (s, 1H), 8.42 (s, 2H), 7.83-7.78 (m, 1H), 7.51-7.45 (m, 1H), 7.39-7.31 (m, 3H), 6.95-6.91 (m, 3H)

Compound 36: 7-(2-Fluorophenyl)-3-(m-tolyl)thieno[3,2-d]pyrimidin-4(3H)-one

In the same manner as the synthesis of Compound 1, methyl 3-amino-4-(2-fluorophenyl)thiophene-2-carboxylate (80 mg, 0.3 mmol), triethyl orthoformate (0.79 ml), m-toluidine (63.8 mg, 0.59 mmol), and acetic acid (0.09 ml) were used to give 70 mg (0.21 mmol, 65.0% yield) of the title compound.

$^1$H NMR (400 MHz, DMSO) δ 8.45-8.43 (m, 2H), 7.85-7.80 (m, 1H), 7.53-7.46 (m, 2H), 7.40-7.33 (m, 5H), 2.41 (s, 3H)

Compound 37: 3-(3-Chlorophenyl)-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (80 mg, 0.3 mmol), triethyl orthoformate (0.79 ml), 3-chloroaniline (75.5 mg, 0.59 mmol), and acetic acid (0.09 ml) were used to give 84 mg (0.24 mmol, 73.6% yield) of the title compound.

$^1$H NMR (400 MHz, DMSO) δ 8.49 (s, 1H), 8.45 (s, 1H), 7.83-7.78 (m, 2H), 7.64-7.52 (m, 3H), 7.50-7.48 (m, 1H), 7.42-7.34 (m, 2H)

Compound 38: 7-(2-Fluorophenyl)-3-(3-vinylphenyl)thieno[3,2-d]pyrimidin-4(3H)-one In the same manner as the synthesis of Compound 1, methyl 3-amino-4-(2-fluorophenyl)thiophene-2-carboxylate (80 mg, 0.3 mmol), triethyl orthoformate (0.79 ml), 3-vinylaniline (70.6 mg, 0.59 mmol), and acetic acid (0.09 ml) were used to give 64 mg (0.18 mmol, 57.4% yield) of the title compound.

$^1$H NMR (400 MHz, DMSO) δ 8.49 (s, 1H), 8.44 (s, 1H), 8.44-7.80 (m, 1H), 7.72 (s, 1H), 7.64 (d, J=7.6 Hz), 7.59-7.34 (m, 3H), 7.40-7.34 (m, 2H), 6.83 (dd, J=17.6, 10.8 Hz, 1H), 5.97 (d, J=17.6 Hz, 1H), 5.39 (d, J=10.8 Hz, 1H)

Compound 39: 3-(7-(2-Fluorophenyl)-4-oxothieno[3,2-d]pyrimidin-3(4H)-yl)benzonitrile In the same manner as the synthesis of Compound 1, methyl 3-amino-4-(2-fluorophenyl)thiophene-2-carboxylate (80 mg, 0.3 mmol), triethyl orthoformate (0.79 ml), 3-aminobenzonitrile (70 mg, 0.59 mmol), and acetic acid (0.09 ml) were used to give 20 mg (0.06 mmol, 18.0% yield) of the title compound.

$^1$H NMR (400 MHz, CDCl$_3$) δ 8.13 (s, 1H), 8.06-8.05 (m, 1H), 7.85-7.80 (m, 3H), 7.73-7.70 (m, 2H), 7.42-7.38 (m, 1H), 7.31-7.27 (m, 1H), 7.25-7.23 (m, 1H)

Compound 40: 3-(4-Chlorophenyl)-7-(3-fluorophenyl)thieno[3,2-d]pyrimidin-4(3H)-one In the same manner as the synthesis of Compound 1, methyl 3-amino-4-(2-fluorophenyl)thiophene-2-carboxylate (50 mg, 0.2 mmol), triethyl orthoformate (0.45 ml), 4-chloroaniline (47.2 mg, 0.37 mmol), and acetic acid (0.05 ml) were used to give 52.1 mg (0.15 mmol, 73.0% yield) of the title compound.

$^1$H NMR (400 MHz, DMSO) δ 8.65 (s, 1H), 8.56 (s, 1H), 7.96-7.88 (m, 2H), 7.69-7.63 (m, 4H), 7.59-7.53 (m, 1H), 7.29-7.24 (m, 1H)

Compound 41: 7-(3-Fluorophenyl)-3-(4-methoxyphenyl)thieno[3,2-d]pyrimidin-4(3H)-one In the same manner as the synthesis of Compound 1, methyl 3-amino-4-(3-fluorophenyl)thiophene-2-carboxylate (56.2 mg, 0.22 mmol), triethyl orthoformate (0.42 ml), p-anisidine (50.5 mg, 0.41 mmol), and acetic acid (0.05 ml) were used to give 30.3 mg (0.086 mmol, 39% yield) of the title compound.

$^1$H NMR (300 MHz, CDCl$_3$) δ 8.22 (s, 1H), 7.95 (s, 1H), 7.68-7.10 (m, 8H), 3.84 (s, 3H)

Compound 42: 3-(4-Chlorophenyl)-7-(4-fluorophenyl)thieno[3,2-d]pyrimidin-4(3H)-one In the same manner as the synthesis of Compound 1, methyl 3-amino-4-(4-fluorophenyl)thiophene-2-carboxylate (80 mg, 0.32 mmol), triethyl orthoformate (2 ml), 4-chloroaniline (74.45 mg, 0.59 mmol), and acetic acid (0.08 ml) were used to give 46 mg (0.13 mmol, 40% yield) of the title compound.

$^1$H NMR (300 MHz, CDCl$_3$) δ 8.52 (s, 1H), 8.45 (s, 1H), 8.08-8.03 (m, 2H), 7.66-7.61 (m, 4H), 7.61-7.32 (m, 2H)

Compound 43: 7-(4-Fluorophenyl)-3-(4-methoxyphenyl)thieno[3,2-d]pyrimidin-4(3H)-one In the same manner as the synthesis of Compound 1, methyl 3-amino-4-(4-fluorophenyl)thiophene-2-carboxylate (80 mg, 0.32 mmol), triethyl orthoformate (2 ml), p-anisidine (72.9 mg, 0.59 mmol), and acetic acid (0.08 ml) were used to give 57 mg (0.16 mmol, 51% yield) of the title compound.

$^1$H NMR (300 MHz, CDCl$_3$) δ 8.5 (s, 1H), 8.48 (s, 1H), 8.08-8.04 (m, 2H), 7.48 (d, J=8.70, 2H), 7.35 (dd, J=8.70, 9.00 Hz, 2H), 7.13 (d, J=2.1 Hz, 2H), 3.84 (s, 3H)

Compound 44: 7-(2-Chlorophenyl)-3-(4-chlorophenyl)thieno[3,2-d]pyrimidin-4(3H)-one In the same manner as the synthesis of Compound 1, methyl 3-amino-4-(2-chlorophenyl)thiophene-2-carboxylate (100 mg, 0.373 mmol), triethyl orthoformate (2 ml), 4-chloroaniline (88.5 mg, 0.70 mmol), and acetic acid (0.1 ml) were used to give 31.3 mg (0.084 mmol, 23% yield) of the title compound.

$^1$H NMR (300 MHz, CDCl$_3$) δ 8.15 (s, 1H), 7.97 (s, 1H), 7.58-7.44 (m, 4H), 7.44-7.40 (m, 4H)

Compound 45: 7-(2-Chlorophenyl)-3-(4-methoxyphenyl)thieno[3,2-d]pyrimidin-4(3H)-one In the same manner as the synthesis of Compound 1, methyl 3-amino-4-(2-chlorophenyl)thiophene-2-carboxylate (100 mg, 0.373 mmol), triethyl orthoformate (2 ml), p-anisidine (85.56 mg, 0.70 mmol), and acetic acid (0.1 ml) were used to give 48.7 mg (0.13 mmol, 35% yield) of the title compound.

$^1$H NMR (300 MHz, CDCl$_3$) δ 8.18 (s, 1H), 7.96 (s, 1H), 7.65-7.54 (m, 2H), 7.45-7.36 (m, 4H), 7.11-7.07 (m, 2H), 3.91 (s, 3H)

Compound 46: 7-(3-Chlorophenyl)-3-(4-chlorophenyl)thieno[3,2-d]pyrimidin-4(3H)-one In the same manner as the synthesis of Compound 1, methyl 3-amino-4-(2-methoxyphenyl)thiophene-2-carboxylate (80 mg, 0.3 mmol), triethyl orthoformate (0.66 ml), 4-chloroaniline (71.2 mg, 0.56 mmol), and acetic acid (0.09 ml) were used to give 78.3 mg (0.21 mmol, 70.8% yield) of the title compound.

$^1$H NMR (400 MHz, CDCl$_3$) δ 8.17 (s, 1H), 7.94 (s, 1H), 7.89-7.88 (m, 1H), 7.75-7.72 (m, 1H), 7.56-7.54 (m, 2H), 7.41-7.39 (m, 4H)

Compound 47: 7-(3-Chlorophenyl)-3-(4-methoxyphenyl)thieno[3,2-d]pyrimidin-4(3H)-one In the same manner as the synthesis of Compound 1, methyl 3-amino-4-(3-chlorophenyl)thiophene-2-carboxylate (80 mg, 0.3 mmol), triethyl orthoformate (0.66 ml), p-anisidine (68.5 mg, 0.56 mmol), and acetic acid (0.09 ml) were used to give 84 mg (0.23 mmol, 76% yield) of the title compound.

$^1$H NMR (400 MHz, CDCl$_3$) δ 8.19 (s, 1H), 7.92 (s, 1H), 7.90-7.89 (m, 1H), 7.76-7.36 (m, 1H), 7.44-7.33 (m, 4H), 7.08-7.04 (m, 2H), 3.88 (s, 3H)

Compound 48: 3,7-Bis(4-chlorophenyl)thieno[3,2-d]pyrimidin-4(3H)-one

In the same manner as the synthesis of Compound 1, methyl 3-amino-4-(4-chlorophenyl)thiophene-2-carboxylate (100 mg, 0.373 mmol), triethyl orthoformate (2 ml), 4-chloroaniline (88.5 mg, 0.70 mmol), and acetic acid (0.1 ml) were used to give 15 mg (0.04 mmol, 11% yield) of the title compound.

$^1$H NMR (300 MHz, CDCl$_3$) δ 8.15 (s, 1H), 7.90 (s, 1H), 7.81-7.79 (m, 2H), 7.54 (d, J=6.3 Hz, 2H), 7.46 (d, J=6.3 Hz, 2H), 7.39 (d, J=6.9 Hz, 2H)

Compound 49: 7-(4-Chlorophenyl)-3-(4-methoxyphenyl)thieno[3,2-d]pyrimidin-4(3H)-one In the same manner as the synthesis of Compound 1, methyl 3-amino-4-(4-chlorophenyl)thiophene-2-carboxylate (100 mg, 0.373 mmol), triethyl orthoformate (2 ml), p-anisidine (85.56 mg, 0.70 mmol), and acetic acid (0.1 ml) were used to give 97 mg (0.26 mmol, 70% yield) of the title compound.

$^1$H NMR (300 MHz, CDCl$_3$) δ 8.22 (s, 1H), 7.93 (s, 1H), 7.87-7.83 (m, 2H), 7.52-7.48 (m, 2H), 7.41-7.36 (m, 2H), 7.12-7.07 (m, 2H), 3.92 (s, 3H)

Compound 50: 7-(2-Bromophenyl)-3-(4-chlorophenyl)thieno[3,2-d]pyrimidin-4(3H)-one In the same manner as the synthesis of Compound 1, methyl 3-amino-4-(2-bromophenyl)thiophene-2-carboxylate (150 mg, 0.48 mmol), triethyl orthoformate (0.64 ml), 4-chloroaniline (75 mg, 0.59 mmol), and acetic acid (0.08 ml) were used to give 148.2 mg (0.35 mmol, 73% yield) of the title compound.

$^1$H NMR (300 MHz, CDCl$_3$) δ 8.13 (s, 1H), 7.93 (s, 1H), 7.45 (d, J=8.1 Hz, 1H), 7.24-7.04 (m, 7H)

Compound 51: 7-(2-Bromophenyl)-3-(4-methoxyphenyl)thieno[3,2-d]pyrimidin-4(3H)-one In the same manner as the synthesis of Compound 1, methyl 3-amino-4-(2-bromophenyl)thiophene-2-carboxylate (1.4 g, 4.48 mmol), triethyl orthoformate (12 ml), p-anisidine (930 mg, 8.52 mmol), and acetic acid (1.2 ml) were used to give 422 mg (1.02 mmol, 23% yield) of the title compound.

$^1$H NMR (300 MHz, DMSO) δ 8.37 (s, 1H), 7.33 (s, 1H), 7.79 (d, J=5.8 Hz, 1H), 7.53-7.46 (m, 4H), 7.42-7.38 (m, 1H), 7.13-7.09 (m, 3H), 3.84 (s, 3H)

Compound 52: 7-(2-Iodophenyl)-3-(4-methoxyphenyl)thieno[3,2-d]pyrimidin-4(3H)-one In the same manner as the synthesis of Compound 1, methyl 3-amino-4-(2-iodophenyl)thiophene-2-carboxylate (700 mg, 1.95 mmol), triethyl orthoformate (3 ml), p-anisidine (231 mg, 2.12 mmol), and acetic acid (0.3 ml) were used to give 460 mg (1.00 mmol, 51% yield) of the title compound.

$^1$H NMR (400 MHz, CDCl$_3$) δ 8.37 (s, 1H), 8.28 (s, 1H), 8.02 (dd, J=8.0, 1.2 Hz, 1H), 7.54-7.46 (m, 3H), 7.42 (dd, J=7.6, 1.6 Hz, 1H), 7.21 (td, J=7.6, 1.6 Hz, 1H), 7.13-7.093 (m, 2H)

Compound 53: 3-(4-Methoxyphenyl)-7-(2-(trimethylstannyl)phenyl)thieno[3,2-d]pyrimidin-4(3H)-one 7-(2-Iodophenyl)-3-(4-methoxyphenyl)thieno[3,2-d]pyrimidin-4(3H)-one (300 mg, 0.65 mmol), hexamethylditin (427 mg, 1.30 mmol), Pd(PPh$_3$)$_4$ (150 mg, 0.13 mmol), and Ag$_2$O (302 mg, 1.30 mmol) were dissolved in dry toluene (4 ml) in a reaction vessel. The oxygen content of the mixture was maximized using argon gas and an aspirator. Thereafter, the mixture was stirred at 100° C. for 16 hr. After completion of the reaction, the reaction mixture was cooled to room temperature and purified by silica gel column chromatography (EtOAc:Hex=1:3) to give 200 mg (0.40 mmol, 62% yield) of the title compound.

$^1$H NMR (400 MHz, CDCl$_3$) δ 8.38 (s, 1H), 8.13 (s, 1H), 7.61-7.59 (m, 1H), 7.48-7.38 (m, 5H), 7.13-7.11 (m, 2H), 3.85 (s, 3H), 0.00 (quint, J=27.6 Hz, 9H)

Compound 54: 3-(4-Chlorophenyl)-7-(o-tolyl)thieno[3,2-d]pyrimidin-4(3H)-one

In the same manner as the synthesis of Compound 1, methyl 3-amino-4-(o-tolyl)thiophene-2-carboxylate (80 mg, 0.32 mmol), triethyl orthoformate (0.7 ml), 4-chloroaniline (76.8 mg, 0.6 mmol), and acetic acid (0.1 ml) were used to give 33.5 mg (0.09 mmol, 28.4% yield) of the title compound.

$^1$H NMR (400 MHz, CDCl$_3$) δ 8.09 (s, 1H), 7.73 (s, 1H), 7.54-7.52 (m, 2H), 7.40-7.38 (m, 2H), 7.35-7.31 (m, 4H), 2.28 (s, 3H)

Compound 55: 3-(4-Methoxyphenyl)-7-(o-tolyl)thieno[3,2-d]pyrimidin-4(3H)-one In the same manner as the synthesis of Compound 1, methyl 3-amino-4-(o-tolyl)thiophene-2-carboxylate (100 mg, 0.4 mmol), triethyl orthoformate (0.88 ml), p-anisidine (92.6 mg, 0.75 mmol), and acetic acid (0.13 ml) were used to give 83.2 mg (0.24 mmol, 60% yield) of the title compound.

$^1$H NMR (400 MHz, CDCl$_3$) δ 8.11 (s, 1H), 7.70 (s, 1H), 7.36-7.30 (m, 6H), 7.04 (d, J=2 Hz, 2H), 3.87 (s, 3H), 2.28 (s, 3H)

Compound 56: 3-(4-Chlorophenyl)-7-(m-tolyl)thieno[3,2-d]pyrimidin-4(3H)-one

In the same manner as the synthesis of Compound 1, methyl 3-amino-4-(m-tolyl)thiophene-2-carboxylate (80 mg, 0.32 mmol), triethyl orthoformate (0.7 ml), 4-chloroaniline (76.8 mg, 0.6 mmol), and acetic acid (0.1 ml) were used to give 85.1 mg (0.23 mmol, 72.1% yield) of the title compound.

$^1$H NMR (300 MHz, CDCl$_3$) δ 8.15 (s, 1H), 7.88 (s, 1H), 7.63-7.61 (m, 2H), 7.55-7.51 (m, 2H), 7.41-7.35 (m, 3H), 2.44 (s, 3H)

Compound 57: 3-(4-Methoxyphenyl)-7-(m-tolyl)thieno[3,2-d]pyrimidin-4(3H)-one

In the same manner as the synthesis of Compound 1, methyl 3-amino-4-(m-tolyl)thiophene-2-carboxylate (80 mg, 0.32 mmol), triethyl orthoformate (0.7 ml), p-anisidine (74.1 mg, 0.6 mmol), and acetic acid (0.1 ml) were used to give 36.5 mg (0.11 mmol, 32.7% yield) of the title compound.

$^1$H NMR (300 MHz, CDCl$_3$) δ 8.17 (s, 1H), 7.86 (s, 1H), 7.63-7.62 (m, 2H), 7.37-7.33 (m, 3H), 7.22-7.20 (m, 1H), 7.06-7.03 (m, 2H), 3.87 (s, 3H), 2.44 (s, 3H)

Compound 58: 3-(4-Chlorophenyl)-7-(p-tolyl)thieno[3,2-d]pyrimidin-4(3H)-one

In the same manner as the synthesis of Compound 1, methyl 3-amino-4-(p-tolyl)thiophene-2-carboxylate (100 mg, 0.40 mmol), triethyl orthoformate (1 ml), 4-chloroaniline (94.4 mg, 0.74 mmol), and acetic acid (0.1 ml) were used to give 48 mg (0.14 mmol, 35% yield) of the title compound.

$^1$H NMR (300 MHz, CDCl$_3$) δ 8.19 (s, 1H), 7.90 (s, 1H), 7.78 (d, J=8.1 Hz, 2H), 7.59-7.56 (m, 2H), 7.46-7.42 (m, 2H), 7.35-7.30 (m, 2H), 2.46 (s, 3H)

Compound 59: 3-(4-Methoxyphenyl)-7-(p-tolyl)thieno[3,2-d]pyrimidin-4(3H)-one

In the same manner as the synthesis of Compound 1, methyl 3-amino-4-(p-tolyl)thiophene-2-carboxylate (100 mg, 0.40 mmol), triethyl orthoformate (1 ml), p-anisidine (91.63 mg, 0.74 mmol), and acetic acid (0.1 ml) were used to give 98.3 mg (0.28 mmol, 70% yield) of the title compound.

$^1$H NMR (300 MHz, CDCl$_3$) δ 8.21 (s, 1H), 7.88 (s, 1H), 7.78-7.75 (m, 2H), 7.41-7.33 (m, 4H), 7.11-7.08 (m, 2H), 3.92 (s, 3H), 2.45 (s, 3H)

Compound 60: 3-(4-Chlorophenyl)-7-(2-methoxyphenyl)thieno[3,2-d]pyrimidin-4(3H)-one In the same manner as the synthesis of Compound 1, methyl 3-amino-4-(2-methoxyphenyl)thiophene-2-carboxylate (50 mg, 0.21 mmol), triethyl orthoformate (0.41 ml), 4-chloroaniline (45.05 mg, 0.35 mmol), and acetic acid (0.05 ml) were used to give 49.4 mg (0.13 mmol, 70.5% yield) of the title compound.

$^1$H NMR (300 MHz, CDCl$_3$) δ 8.12 (s, 1H), 8.01 (s, 1H), 7.65-7.62 (m, 1H), 7.55-7.51 (m, 2H), 7.43-7.37 (m, 3H), 7.12-7.04 (m, 2H), 3.85 (s, 1H)

Compound 61: 7-(2-Methoxyphenyl)-3-(4-methoxyphenyl)thieno[3,2-d]pyrimidin-4(3H)-one In the same manner as the synthesis of Compound 1, methyl 3-amino-4-(2-methoxyphenyl)thiophene-2-carboxylate (40 mg, 0.15 mmol), triethyl orthoformate (0.33 ml), p-anisidine (34.8 mg, 0.28 mmol), and acetic acid (0.04 ml) were used to give 31 mg (0.09 mmol, 56.7% yield) of the title compound.

$^1$H NMR (400 MHz, CDCl$_3$) δ 8.14 (s, 1H), 7.99 (s, 1H), 7.65 (dd, J=7.6, 1.6 Hz, 1H) 7.41-7.33 (m, 3H), 7.11-7.03 (m, 4H), 3.87 (s, 3H), 3.85 (s, 3H)

Compound 62: 3-(4-Chlorophenyl)-7-(3-methoxyphenyl)thieno[3,2-d]pyrimidin-4(3H)-one In the same manner as the synthesis of Compound 1, methyl 3-amino-4-(3-methoxyphenyl)thiophene-2-carboxylate (80 mg, 0.3 mmol), triethyl orthoformate (0.66 ml), 4-chloroaniline (72.1 mg, 0.57 mmol), and acetic acid (0.08 ml) were used to give 13.2 mg (0.04 mmol, 11.9% yield) of the title compound.

$^1$H NMR (400 MHz, CDCl$_3$) δ 8.16 (s, 1H), 7.92 (s, 1H), 7.54 (dd, J=6.8, 2 Hz, 2H), 7.43-7.39 (m, 3H), 6.96-6.94 (m, 1H), 3.88 (s, 3H)

Compound 63: 7-(3-Methoxyphenyl)-3-(4-methoxyphenyl)thieno[3,2-d]pyrimidin-4(3H)-one In the same manner as the synthesis of Compound 1, methyl 3-amino-4-(3-methoxyphenyl)thiophene-2-carboxylate (80 mg, 0.3 mmol), triethyl orthoformate (0.66 ml), p-anisidine (70.2 mg, 0.57 mmol), and acetic acid (0.08 ml) were used to give 56 mg (0.15 mmol, 51.2% yield) of the title compound.

$^1$H NMR (400 MHz, CDCl$_3$) δ 8.18 (s, 1H), 7.89 (s, 1H), 7.44-7.40 (m, 3H), 7.36-7.34 (m, 2H), 7.06-7.04 (m, 2H), 6.98-6.93 (m, 1H), 3.88 (s, 6H)

Compound 64: 3-(4-Chlorophenyl)-7-(4-methoxyphenyl)thieno[3,2-d]pyrimidin-4(3H)-one In the same manner as the synthesis of Compound 1, methyl 3-amino-4-(4-methoxyphenyl)thiophene-2-carboxylate (80 mg, 0.3 mmol), triethyl orthoformate (0.66 ml), 4-chloroaniline (71.2 mg, 0.56 mmol), and acetic acid (0.08 ml) were used to give 96.2 mg (0.26 mmol, 86.9% yield) of the title compound.

$^1$H NMR (400 MHz, CDCl$_3$) δ 8.15 (s, 1H), 7.82 (s, 1H), 7.77 (d, J=8.8 Hz, 2H), 7.54 (d, J=8.8 Hz, 2H), 7.39 (d, J=8.8 Hz, 2H), 7.02 (d, J=8.8 Hz, 2H), 3.86 (s, 3H)

Compound 65: 3,7-Bis(4-methoxyphenyl)thieno[3,2-d]pyrimidin-4(3H)-one

In the same manner as the synthesis of Compound 1, methyl 3-amino-4-(4-methoxyphenyl)thiophene-2-carboxylate (80 mg, 0.3 mmol), triethyl orthoformate (0.66 ml), p-anisidine (70.2 mg, 0.57 mmol), and acetic acid (0.08 ml) were used to give 95.7 mg (0.26 mmol, 87.5% yield) of the title compound.

¹H NMR (400 MHz, CDCl₃) δ 8.47 (s, 1H), 8.39 (s, 1H), 7.97 (d, J=8.8 Hz, 2H), 7.5 (d, J=8.8 Hz, 2H), 7.13 (d, J=8.8 Hz, 2H), 7.07 (d, J=8.8 Hz, 2H), 3.85 (s, 3H), 3.83 (s, 3H)

Compound 66: 3-(4-Chlorophenyl)-7-(3,4-dimethoxyphenyl)thieno[3,2-d]pyrimidin-4(3H)-one In the same manner as the synthesis of Compound 1, methyl 3-amino-4-(3,4-dimethoxyphenyl)thiophene-2-carboxylate (30 mg, 0.13 mmol), triethyl orthoformate (0.31 ml), 4-chloroaniline (29.7 mg, 0.23 mmol), and acetic acid (0.04 ml) were used to give 14.5 mg (0.04 mmol, 28% yield) of the title compound.
¹H NMR (400 MHz, CDCl₃) δ 8.16 (s, 1H), 7.85 (s, 1H), 7.55-7.53 (m, 2H), 7.47 (d, J=8 Hz, 4H), 7.00 (d, J=8 Hz, 2H), 3.95 (d, J=8 Hz, 6H)

Compound 67: 7-(3,4-Dimethoxyphenyl)-3-(4-methoxyphenyl)thieno[3,2-d]pyrimidin-4(3H)-one In the same manner as the synthesis of Compound 1, methyl 3-amino-4-(3,4-dimethoxyphenyl)thiophene-2-carboxylate (80 mg, 0.27 mmol), triethyl orthoformate (0.6 ml), 4-chloroaniline (62.5 mg, 0.51 mmol), and acetic acid (0.09 ml) were used to give 14.5 mg (0.04 mmol, 28% yield) of the title compound.
¹H NMR (400 MHz, CDCl₃) δ 8.18 (s, 1H), 7.82 (s, 1H), 7.43-7.39 (m, 2H), 7.35 (dd, J=6.8, 2 Hz, 2H), 7.05 (dd, J=6.8, 2 Hz, 2H), 6.99 (d, J=8 Hz, 1H), 3.97 (d, J=9.6 Hz, 6H), 3.88 (s, 3H)

Compound 68: 7-(Benzo[d][1,3]dioxol-5-yl)-3-(4-chlorophenyl)thieno[3,2-d]pyrimidin-4(3H)-one In the same manner as the synthesis of Compound 1, methyl 3-amino-4-(benzo[d][1,3]dioxol-5-yl)thiophene-2-carboxylate (60 mg, 0.21 mmol), triethyl orthoformate (0.48 ml), 4-chloroaniline (51.0 mg, 0.4 mmol), and acetic acid (0.06 ml) were used to give 47.3 mg (0.17 mmol, 79.5% yield) of the title compound.
¹H NMR (300 MHz, CDCl₃) δ 8.14 (s, 1H), 8.13 (s, 1H), 7.55-7.52 (m, 2H), 7.41-7.35 (m, 3H), 7.03 (d, J=10.4 Hz, 1H), 6.93 (d, J=10.8 Hz, 1H), 6.02 (s, 2H)

Compound 69: 7-(Benzo[d][1,3]dioxol-5-yl)-3-(4-methoxyphenyl)thieno[3,2-d]pyrimidin-4(3H)-one In the same manner as the synthesis of Compound 1, methyl 3-amino-4-(benzo[d][1,3]dioxol-5-yl)thiophene-2-carboxylate (60 mg, 0.21 mmol), triethyl orthoformate (0.46 ml), p-anisidine (49.6 mg, 0.4 mmol), and acetic acid (0.06 ml) were used to give 52.4 mg (0.14 mmol, 65.2% yield) of the title compound.
¹H NMR (400 MHz, DMSO) δ 8.47 (s, 1H), 8.42 (s, 1H), 7.60-7.56 (m, 2H), 7.30 (dd, J=146.6, 8.86 Hz, 4H), 7.05 (d, J=8.08 Hz, 1H), 6.09 (s, 2H), 3.84 (s, 3H)

Compound 70: 3-(4-Chlorophenyl)-7-(naphthalen-1-yl)thieno[3,2-d]pyrimidin-4(3H)-one In the same manner as the synthesis of Compound 1, methyl 3-amino-4-(naphthalen-1-yl)thiophene-2-carboxylate (43.8 mg, 0.15 mmol), triethyl orthoformate (0.32 ml), 4-chloroaniline (44.3 mg, 0.4 mmol), and acetic acid (0.04 ml) were used to give 27 mg (0.07 mmol, 46.3% yield) of the title compound.
¹H NMR (300 MHz, CDCl₃) δ 8.05 (s, 1H), 7.95-7.91 (m, 3H), 7.74 (d, J=12 Hz, 1H), 7.61-7.38 (m, 8H)

Compound 71: 3-(4-Methoxyphenyl)-7-(naphthalen-1-yl)thieno[3,2-d]pyrimidin-4(3H)-one In the same manner as the synthesis of Compound 1, methyl 3-amino-4-(naphthalen-1-yl)thiophene-2-carboxylate (60 mg, 0.21 mmol), triethyl orthoformate (0.46 ml), p-anisidine (48.5 mg, 0.39 mmol), and acetic acid (0.06 ml) were used to give 42.8 mg (0.12 mmol, 58.5% yield) of the title compound.
¹H NMR (300 MHz, CDCl₃) δ 8.01 (s, 1H), 7.96-7.92 (m, 2H), 7.89 (s, 1H), 7.76 (d, J=8 Hz, 1H) 7.62-7.37 (m, 4H), 7.35-7.33 (m, 2H), 7.07-7.02 (m, 2H), 3.87 (s, 3H)

Compound 72: 3-(4-Chlorophenyl)-7-(naphthalen-2-yl)thieno[3,2-d]pyrimidin-4(3H)-one In the same manner as the synthesis of Compound 1, methyl 3-amino-4-(naphthalen-2-yl)thiophene-2-carboxylate (43.8 mg, 0.15 mmol), triethyl orthoformate (0.32 ml), 4-chloroaniline (36.7 mg, 0.28 mmol), and acetic acid (0.04 ml) were used to give 100 mg (0.26 mmol, 92% yield) of the title compound.
¹H NMR (300 MHz, CDCl₃) δ 8.37 (s, 1H), 8.13 (s, 1H), 7.96-7.85 (m, 5H), 7.52-7.48 (m, 4H), 7.38-7.35 (m, 2H)

Compound 73: 3-(4-Methoxyphenyl)-7-(naphthalen-2-yl)thieno[3,2-d]pyrimidin-4(3H)-one In the same manner as the synthesis of Compound 1, methyl 3-amino-4-(naphthalen-2-yl)thiophene-2-carboxylate (80 mg, 0.28 mmol), triethyl orthoformate (0.62 ml), p-anisidine (64.7 mg, 0.53 mmol), and acetic acid (0.08 ml) were used to give 36.5 mg (0.1 mmol, 33.9% yield) of the title compound.
¹H NMR (400 MHz, CDCl₃) δ 8.40 (s, 1H), 8.23 (s, 1H), 8.01 (s, 1H), 7.95-7.87 (m, 4H), 7.53-7.51 (m, 3H), 7.37 (d, J=8.8 Hz, 2H), 7.01 (d, J=8.8 Hz, 2H), 3.89 (s, 3H)

Compound 74: 3-(4-Methoxyphenyl)-2-methyl-7-phenylthieno[3,2-d]pyrimidin-4(3H)-one 3-Amino-N-(4-methoxyphenyl)-4-phenylthiophene-2-carboxamide (57 mg, 0.18 mmol), triethyl orthoacetate (1 ml), and acetic acid (0.1 ml) were placed in a pressure bottle. The mixture was heated with stirring at 160° C. for 18 hr. After the completion of the reaction was confirmed by TLC, the reaction mixture was cooled to room temperature and solidified with diethyl ether and EtOAc to give 13 mg (0.037 mmol, 21% yield) of the title compound.
¹H NMR (300 MHz, DMSO) δ 8.43 (s, 1H), 8.01 (d, J=7.5 Hz, 2H), 7.52-7.37 (m, 5H), 7.11 (d, J=8.7 Hz, 2H) 3.84 (s, 3H), 2.19 (s, 3H)

Compound 75: 3-(4-Chlorophenyl)-7-phenylthieno[3,2-d]pyrimidin-2,4(1H,3H)-dione

Methyl 3-amino-4-phenylthiophene-2-carboxylate (400 mg, 1.71 mmol), triethylamine (0.04 ml, 0.43 mmol), and 4-chlorophenyl isocyanate (0.39 ml, 3.16 mmol) were dissolved in 1,4-dioxane (10 ml) in a reaction vessel. The mixture was heated with stirring at 90° C. for 3 days. After the completion of the reaction was confirmed by TLC, the reaction mixture was cooled to room temperature and filtered. The filtered solid was dissolved in a 10% sodium hydroxide/ methanol (3 ml/12 ml) solution and refluxed with stirring at 100° C. overnight. After completion of the reaction, the reaction solution was cooled to room temperature, acidified with 3 N hydrochloric acid, and filtered to give 548 mg (1.54 mmol, 90% yield) of the title compound as a solid.

¹H NMR (300 MHz, CDCl₃) δ 7.74 (s, 1H), 7.65 (s, 1H), 7.45-7.61 (m, 7H), 7.27-7.30 (m, 2H)

0.43 mmol), triethyl orthoformate (1.0 ml), allylamine hydrochloride (92.6 mg, 0.99 mmol), and acetic acid (0.1 ml) were used to give 66.4 mg (0.25 mmol, 57.5% yield) of the title compound.

¹H NMR (300 MHz, CDCl₃) δ 8.11 (s, 1H), 7.84-7.79 (m, 3H), 7.50-7.44 (m, 2H), 7.41-7.36 (m, 1H), 6.08-5.95 (m, 1H), 5.34-5.24 (m, 2H), 4.72-4.67 (m, 2H)

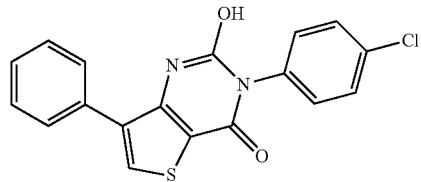 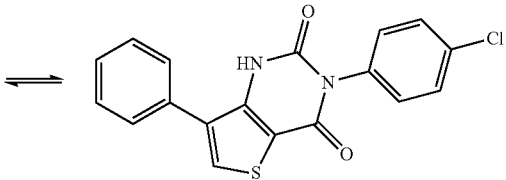

Compound 76: 3-(4-Chlorophenyl)-2-(dimethylamino)-7-phenylthieno[3,2-d]pyrimidin-4(3H)-one 3-(4-Chlorophenyl)-7-phenylthieno[3,2-d]pyrimidin-2,4 (1H,3H)-dione (100 mg, 0.3 mmol), N,N-diethylaniline (0.014 ml, 0.09 mmol), and phosphoryl chloride (0.34 ml, 3.6 mmol) were placed in a reaction vessel. The mixture was heated with stirring at 130° C. overnight. After the completion of the reaction was confirmed by TLC, the reaction mixture was cooled to room temperature and separated with NaHCO₃ and dichloromethane. The extracted organic layer was washed with brine, dried over anhydrous MgSO₄, and filtered. The filtrate was distilled under reduced pressure. The concentrate was purified by silica gel column chromatography (EtOAc:Hex=1:5) to give 2-chloro-3-(4-chlorophenyl)-7-phenyl-2,3-dihydrothieno[3,2-d]pyrimidin-4(1H)-one (22.7 mg, 0.06 mmol, 20% yield).

The thus synthesized compound 2-chloro-3-(4-chlorophenyl)-7-phenyl-2,3-dihydrothieno[3,2-d]pyrimidin-4(1H)-one (22.7 mg, 0.06 mmol) was mixed with a solution of N,N-dimethylamine (3 ml) and diisopropylethylamine (0.01 ml, 0.06 mmol) in THF. The mixture was heated with stirring at 65° C. overnight. After the completion of the reaction was confirmed by TLC, the reaction mixture was cooled to room temperature and separated with water and dichloromethane. The extracted organic layer was washed with brine, dried over anhydrous MgSO₄, and filtered. The filtrate was distilled under reduced pressure. The concentrate was purified by silica gel column chromatography (EtOAc:Hex=1:5) to give 14.1 mg (0.037 mmol, 62% yield) of the title compound.

¹H NMR (300 MHz, CDCl₃) δ 8.00-7.97 (m, 2H), 7.84 (s, 1H), 7.52-7.30 (m, 8H), 2.69 (s, 6H)

Compound 77: 3-Butyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), n-butylamine (0.097 ml, 0.99 mmol), and acetic acid (0.1 ml) were used to give 92 mg (0.32 mmol, 75.2% yield) of the title compound.

¹H NMR (400 MHz, CDCl₃) δ 8.10 (s, 1H), 7.82-7.79 (m, 3H), 7.49-7.56 (m, 2H), 7.40-7.36 (m, 1H), 4.07 (t, J=7.3 Hz, 2H), 1.84-1.76 (m, 2H), 1.42 (sextet, J=7.5 Hz, 2H), 0.97 (t, J=7.4 Hz, 3H)

Compound 78: 3-Allyl-7-phenylthieno[3,2-d]pyrimidin-4(3H)-one

In the same manner as the synthesis of Compound 1, methyl 3-amino-4-phenylthiophene-2-carboxylate (100 mg, Compound 79: 3-Cyclobutyl-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), cyclobutylamine (0.084 ml, 0.99 mmol), and acetic acid (0.1 ml) were used to give 83.9 mg (0.30 mmol, 69.1% yield) of the title compound.

¹H NMR (400 MHz, CDCl₃) δ 8.27 (s, 1H), 7.82-7.79 (m, 3H), 7.49-7.45 (m, 2H), 7.40-7.36 (m, 1H), 5.17-5.09 (m, 1H), 2.63-2.56 (m, 2H), 2.44-2.32 (m, 2H), 1.99-1.91 (m, 2H)

Compound 80: 3-Cyclopentyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), cyclopentylamine (0.080 ml, 0.81 mmol), and acetic acid (0.1 ml) were used to give 108.3 mg (0.37 mmol, 85% yield) of the title compound.

¹H NMR (400 MHz, CDCl₃) δ 8.21 (s, 1H), 7.82-7.79 (m, 3H), 7.49-7.45 (m, 2H), 7.40-7.36 (m, 1H), 5.30-5.23 (m, 1H), 2.31-2.22 (m, 2H), 1.99-1.75 (m, 6H), 1.57-1.54 (m, 2H)

Compound 81: 3-Cyclohexyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), cyclohexylamine (0.113 ml, 0.99 mmol), and acetic acid (0.1 ml) were used to give 109.7 mg (0.35 mmol, 82.2% yield) of the title compound.

¹H NMR (400 MHz, CDCl₃) δ 8.20 (s, 1H), 7.82-7.79 (m, 3H), 7.49-7.44 (m, 2H), 7.40-7.36 (m, 1H), 4.91-4.84 (m, 1H), 2.05 (d, J=12.0 Hz, 2H), 1.95 (d, J=13.2 Hz, 2H), 1.81-1.78 (m, 1H), 1.68-1.48 (m, 4H), 1.32-1.21 (m, 1H)

Compound 82: 3-Cyclooctyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), cyclooctylamine (0.113 ml, 0.81 mmol), and acetic acid (0.1 ml) were used to give 82.9 mg (0.24 mmol, 57% yield) of the title compound.

¹H NMR (400 MHz, CDCl₃) δ 8.19 (s, 1H), 7.82-7.79 (m, 3H), 7.49-7.44 (m, 2H), 7.40-7.36 (m, 1H), 5.17-5.10 (m, 1H), 2.04-1.94 (m, 4H), 1.87-1.83 (m, 2H), 1.74-1.60 (m, 8H)

Compound 83: 3-(Cyclopropylmethyl)-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), cyclopropanemethylamine (0.086 ml, 0.99 mmol), and acetic acid (0.1 ml) were used to give 76 mg (0.27 mmol, 62.6% yield) of the title compound.
$^1$H NMR (400 MHz, CDCl$_3$) δ 8.19 (s, 1H), 7.83-7.79 (m, 3H), 7.49-7.45 (m, 2H), 7.40-7.36 (m, 1H), 3.93 (d, J=7.2 Hz, 2H), 1.37-1.25 (m, 1H), 0.71-0.59 (m, 2H), 0.50-0.39 (m, 2H)

Compound 84: 3-(Cyclohexylmethyl)-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), cyclohexanemethylamine (0.129 ml, 0.99 mmol), and acetic acid (0.1 ml) were used to give 102.3 mg (0.32 mmol, 73.3% yield) of the title compound.
$^1$H NMR (400 MHz, CDCl$_3$) δ 8.04 (s, 1H), 7.82-7.79 (m, 3H), 7.49-7.45 (m, 2H), 7.40-7.36 (m, 1H), 3.77 (d, J=7.3 Hz, 2H), 1.95-1.84 (m, 1H), 1.74-1.67 (m, 5H), 1.29-1.12 (m, 3H), 1.07-0.98 (m, 2H)

Compound 85: 3-((1R,4R)-4-methylcyclohexyl)-7-phenylthieno[3,2-d]pyrimidin-4(3H)-one In the same manner as the synthesis of Compound 1, methyl 3-amino-4-phenylthiophene-2-carboxylate (76 mg, 0.33 mmol), triethyl orthoformate (1.0 ml), trans-4-methylcyclohexylamine (0.1 ml, 0.76 mmol), and acetic acid (0.1 ml) were used to give 53.9 mg (0.17 mmol, 50.3% yield) of the title compound.
$^1$H NMR (400 MHz, CDCl$_3$) δ 8.20 (s, 1H), 7.84-7.79 (m, 3H), 7.49-7.45 (m, 2H), 7.40-7.36 (m, 1H), 4.90-4.82 (m, 1H), 2.05-2.01 (m, 2H), 1.92-1.88 (m, 2H), 1.75-1.64 (m, 2H), 1.55-1.44 (m, 1H), 1.31-1.21 (m, 2H), 0.98 (d, J=6.5 Hz, 3H)

Compound 86: 7-Phenyl-3-(tetrahydro-2H-pyran-4-yl)thieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), 4-aminotetrahydropyrane (0.102 ml, 0.99 mmol), and acetic acid (0.1 ml) were used to give 76.7 mg (0.25 mmol, 57.1% yield) of the title compound.
$^1$H NMR (400 MHz, CDCl$_3$) δ 8.22 (s, 1H), 7.85 (s, 1H), 7.82-7.79 (m, 2H), 7.50-7.46 (m, 2H), 7.41-7.37 (m, 1H), 5.21-5.13 (m, 1H), 4.18-4.14 (m, 2H), 3.63 (td, J=11.4, 2.7 Hz, 2H), 2.08-1.96 (m, 4H)

Compound 87: (R)-7-phenyl-3-(1,2,3,4-tetrahydronaphthalen-1-yl)thieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), (R)-1,2,3,4-tetrahydronaphthalen-1-amine (0.141 ml, 0.99 mmol), and acetic acid (0.1 ml) were used to give 73.3 mg (0.20 mmol, 47.6% yield) of the title compound.
$^1$H NMR (400 MHz, CDCl$_3$) δ 7.86 (s, 1H), 7.81-7.77 (m, 3H), 7.46-7.41 (m, 2H), 7.37-7.33 (m, 1H), 7.24-7.20 (m, 2H), 7.17-7.13 (m, 1H), 6.99-6.97 (m, 1H), 6.29 (t, J=6.0 Hz, 1H), 3.01-2.84 (m, 2H), 2.37-2.28 (m, 1H), 2.13-2.05 (m, 1H), 1.98-1.85 (m, 2H)

Compound 88: (S)-7-phenyl-3-(1,2,3,4-tetrahydronaphthalen-1-yl)thieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), (S)-1,2,3,4-tetrahydronaphthalen-1-amine (0.141 ml, 0.99 mmol), and acetic acid (0.1 ml) were used to give 82.1 mg (0.23 mmol, 53.3% yield) of the title compound.
$^1$H NMR (400 MHz, CDCl$_3$) δ 7.87 (s, 1H), 7.81-7.77 (m, 3H), 7.46-7.41 (m, 2H), 7.37-7.33 (m, 1H), 7.26-7.20 (m, 2H), 7.17-7.13 (m, 1H), 6.98-6.97 (m, 1H), 6.29 (t, J=6.0 Hz, 1H), 3.01-2.84 (m, 2H), 2.36-2.28 (m, 1H), 2.13-2.04 (m, 1H), 1.97-1.85 (m, 2H)

Compound 89: (S)-7-phenyl-3-((tetrahydrofuran-2-yl)methyl)thieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), (S)-(tetrahydrofuran-2-yl)methanamine (0.102 ml, 0.99 mmol), and acetic acid (0.1 ml) were used to give 90.1 mg (0.29 mmol, 67.1% yield) of the title compound.
$^1$H NMR (400 MHz, CDCl$_3$) δ 8.25 (s, 1H), 7.83-7.80 (m, 3H), 7.49-7.46 (m, 2H), 7.40-7.36 (m, 1H), 4.42 (dd, J=10.3, 2.8 Hz, 1H), 4.27-4.21 (m, 1H), 3.96-3.73 (m, 3H), 2.17-2.07 (m, 1H), 1.97-1.83 (m, 2H), 1.67-1.58 (m, 1H)

Compound 90: (R)-7-phenyl-3-((tetrahydrofuran-2-yl)methyl)thieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), (R)-(tetrahydrofuran-2-yl)methanamine (0.102 ml, 0.99 mmol), and acetic acid (0.1 ml) were used to give 97.3 mg (0.31 mmol, 72.4% yield) of the title compound.
$^1$H NMR (400 MHz, CDCl$_3$) δ 8.25 (s, 1H), 7.83-7.80 (m, 3H), 7.49-7.45 (m, 2H), 7.40-7.36 (m, 1H), 4.42 (dd, J=10.4, 2.8 Hz, 1H), 4.27-4.21 (m, 1H), 3.96-3.73 (m, 3H), 2.17-2.07 (m, 1H), 1.97-1.82 (m, 2H), 1.67-1.58 (m, 1H)

Compound 91: 3-(1-Methylpiperidin-4-yl)-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), 1-methylpiperidin-4-amine (0.124 ml, 0.99 mmol), and acetic acid (0.1 ml) were used to give 47.3 mg (0.15 mmol, 33.8% yield) of the title compound.
$^1$H NMR (400 MHz, CDCl$_3$) δ 8.24 (s, 1H), 7.83-7.78 (m, 3H), 7.49-7.45 (m, 2H), 7.40-7.36 (m, 1H), 4.98-4.90 (m, 1H), 3.03 (d, J=12.2 Hz, 2H), 2.36 (s, 3H), 2.27-2.20 (m, 2H), 2.03-1.98 (m, 4H)

Compound 92: 3-Isobutyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), isobutylamine (0.099 ml, 0.99 mmol), and acetic acid (0.1 ml) were used to give 69.7 mg (0.25 mmol, 57% yield) of the title compound.

$^1$H NMR (400 MHz, CDCl$_3$) δ 8.06 (s, 1H), 7.83-7.80 (m, 3H), 7.50-7.46 (m, 2H), 7.41-7.36 (m, 1H), 3.87 (d, J=7.3 Hz, 2H), 2.31-2.17 (m, 1H), 1.00 (d, J=6.7 Hz, 6H)

Compound 93: 3-Neopentyl-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), neopentylamine (0.117 ml, 0.99 mmol), and acetic acid (0.1 ml) were used to give 45.8 mg (0.15 mmol, 35.7% yield) of the title compound.

$^1$H NMR (400 MHz, CDCl$_3$) δ 8.09 (s, 1H), 7.83-7.80 (m, 3H), 7.50-7.45 (m, 2H), 7.40-7.36 (m, 1H), 3.94 (s, 2H), 1.04 (s, 9H)

Compound 94: 3-(2-Methylcyclohexyl)-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), 2-methylcyclohexanamine (0.120 ml, 0.90 mmol), and acetic acid (0.1 ml) were used to give 65.9 mg (0.20 mmol, 47.2% yield) of the title compound.

$^1$H NMR (400 MHz, CDCl$_3$) δ 8.14 (m, 1H), 7.83-7.81 (m, 3H), 7.49-7.45 (m, 2H), 7.40-7.36 (m, 1H), 5.00 (dt, J=13.2, 3.8 Hz, 0.4H), 4.67 (brs, 0.6H), 2.49-1.23 (m, 9H), 0.88 (d, J=7.2 Hz, 1H), 0.83 (d, J=6.4 Hz, 2H)

Compound 95: 3-(3-Methylcyclohexyl)-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1.0 ml), 3-methylcyclohexanamine (0.120 ml, 0.90 mmol), and acetic acid (0.1 ml) were used to give 98.4 mg (0.30 mmol, 70.5% yield) of the title compound.

$^1$H NMR (400 MHz, CDCl$_3$) δ 8.23 (s, 0.3H), 8.20 (s, 0.7H), 7.83-7.80 (m, 3H), 7.49-7.46 (m, 2H), 7.41-7.35 (m, 1H), 5.19-5.11 (m, 0.3H), 4.95-4.87 (m, 0.7H), 2.28-1.50 (m, 8H), 1.34-1.16 (m, 1H), 1.02-0.92 (m, 3H)

Compound 96: 3-(4-Ethylcyclohexyl)-7-phenylthieno[3,2-d]pyrimidin-4(3H)-one

In the same manner as the synthesis of Compound 1, methyl 3-amino-4-phenylthiophene-2-carboxylate (100 mg, 0.43 mmol), triethyl orthoformate (1.0 ml), 4-ethylcyclohexanamine (0.133 ml, 0.90 mmol), and acetic acid (0.1 ml) were used to give 6.8 mg (0.02 mmol, 4.7% yield) of the title compound.

$^1$H NMR (400 MHz, CDCl$_3$) δ 8.22 (s, 0.6H), 8.19 (s, 0.4H), 7.82-7.79 (m, 3H), 7.48-7.44 (m, 2H), 7.39-7.35 (m, 1H), 4.90-4.79 (m, 1H), 2.07-1.62 (m, 8H), 1.51-1.43 (m, 1H), 1.33-1.16 (m, 2H), 0.95-0.90 (m, 3H)

Compound 97: (1R,4R)-4-(4-oxo-7-phenylthieno[3,2-d]pyrimidin-3(4H)-yl)cyclohexyl acetate In the same manner as the synthesis of Compound 1, methyl 3-amino-4-phenylthiophene-2-carboxylate (100 mg, 0.43 mmol), triethyl orthoformate (1.0 ml), (1r,4r)-4-aminocyclohexyl acetate hydrochloride (174 mg, 0.90 mmol), and acetic acid (0.1 ml) were used to give 73.4 mg (0.20 mmol, 46.3% yield) of the title compound.

$^1$H NMR (400 MHz, CDCl$_3$) δ 8.16 (s, 1H), 7.84-7.79 (m, 3H), 7.49-7.45 (m, 2H), 7.40-7.37 (m, 1H), 4.95-4.89 (m, 1H), 4.84-4.76 (m, 1H), 2.21-2.07 (m, 7H), 1.91-1.62 (m, 4H)

Compound 98: 3-Butyl-7-(2-fluorophenyl)thieno[3,2-d]pyrimidin-4(3H)-one

In the same manner as the synthesis of Compound 1, methyl 3-amino-4-(2-fluorophenyl)thiophene-2-carboxylate (100 mg, 0.40 mmol), triethyl orthoformate (1.0 ml), n-butylamine (0.076 ml, 0.76 mmol), and acetic acid (0.1 ml) were used to give 113.2 mg (0.37 mmol, 93.6% yield) of the title compound.

$^1$H NMR (400 MHz, CDCl$_3$) δ 8.09 (s, 1H), 7.96 (d, J=1.6 Hz, 1H), 7.83 (td, J=7.6, 1.8 Hz, 1H), 7.40-7.35 (m, 1H), 7.28-7.18 (m, 2H), 4.07 (t, J=7.3 Hz, 2H), 1.84-1.77 (m, 2H), 1.51-1.37 (m, 2H), 0.98 (t, J=7.4 Hz, 3H)

Compound 99: 3-Allyl-7-(2-fluorophenyl)thieno[3,2-d]pyrimidin-4(3H)-one

In the same manner as the synthesis of Compound 1, methyl 3-amino-4-(2-fluorophenyl)thiophene-2-carboxylate (100 mg, 0.40 mmol), triethyl orthoformate (1.0 ml), allylamine (86 mg, 0.92 mmol), and acetic acid (0.1 ml) were used to give 11.7 mg (0.04 mmol, 10.2% yield) of the title compound.

$^1$H NMR (400 MHz, CDCl$_3$) δ 8.09 (s, 1H), 7.97 (d, J=1.6 Hz, 1H), 7.83 (td, J=7.6, 1.8 Hz, 1H), 7.40-7.35 (m, 1H), 7.28-7.17 (m, 2H), 6.06-5.97 (m, 1H), 5.34-5.26 (m, 2H), 4.71-4.69 (m, 2H)

Compound 100: 3-Cyclobutyl-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclobutylamine (0.065 ml, 0.76 mmol), and acetic acid (0.1 ml) were used to give 110.2 mg (0.37 mmol, 91.7% yield) of the title compound.

$^1$H NMR (400 MHz, CDCl$_3$) δ 8.26 (s, 1H), 7.95 (d, J=1.6 Hz, 1H), 7.83 (td, J=7.6, 1.8 Hz, 1H), 7.40-7.35 (m, 1H), 7.28-7.18 (m, 2H), 5.17-5.08 (m, 1H), 2.64-2.56 (m, 2H), 2.43-2.32 (m, 2H), 1.99-1.91 (m, 2H)

Compound 101: 3-Cyclopentyl-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclopentylamine (0.09 ml, 0.92 mmol), and acetic acid (0.1 ml) were used to give 75 mg (0.24 mmol, 59.7% yield) of the title compound.

$^1$H NMR (400 MHz, CDCl$_3$) δ 8.20 (s, 1H), 7.95 (d, J=1.6 Hz, 1H), 7.82 (td, J=7.6, 1.8 Hz, 1H), 7.40-7.34 (m, 1H), 7.28-7.17 (m, 2H), 5.30-5.22 (m, 1H), 2.30-2.22 (m, 2H), 1.98-1.75 (m, 6H)

Compound 102: 3-Cyclohexyl-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclohexylamine (0.128 ml, 0.92 mmol), and acetic acid (0.1 ml) were used to give 76 mg (0.23 mmol, 57.9% yield) of the title compound.

$^1$H NMR (400 MHz, CDCl$_3$) δ 8.19 (s, 1H), 7.95 (d, J=1.6 Hz, 1H), 7.83 (td, J=7.6, 1.8 Hz, 1H), 7.40-7.34 (m, 1H), 7.28-7.17 (m, 2H), 4.91-4.84 (m, 1H), 2.06-2.03 (m, 2H), 1.96-1.93 (m, 2H), 1.80 (d, J=13.5 Hz, 1H), 1.67-1.48 (m, 4H), 1.32-1.19 (m, 1H)

Compound 103: 3-Cyclooctyl-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclooctylamine (0.128 ml, 0.92 mmol), and acetic acid (0.1 ml) were used to give 90.4 mg (0.25 mmol, 63.4% yield) of the title compound.

$^1$H NMR (400 MHz, CDCl$_3$) δ 8.18 (s, 1H), 7.95 (d, J=1.6 Hz, 1H), 7.83 (td, J=7.6, 1.8 Hz, 1H), 7.41-7.34 (m, 1H), 7.28-7.17 (m, 2H), 5.17-5.10 (m, 1H), 2.05-1.60 (m, 14H)

Compound 104: 3-(Cyclopropylmethyl)-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclopropanemethylamine (0.066 ml, 0.76 mmol), and acetic acid (0.1 ml) were used to give 57.1 mg (0.17 mmol, 43% yield) of the title compound.

$^1$H NMR (400 MHz, CDCl$_3$) δ 8.17 (s, 1H), 7.94 (d, J=1.4 Hz, 1H), 7.82 (td, J=7.6, 1.8 Hz, 1H), 7.38-7.32 (m, 1H), 7.26-7.16 (m, 2H), 3.91 (d, J=7.2 Hz, 2H), 1.34-1.22 (m, 1H), 0.69-0.57 (m, 2H), 0.48-0.37 (m, 2H)

Compound 105: 3-(Cyclohexanemethyl)-7-(2-fluorophenyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), cyclohexanemethylamine (0.099 ml, 0.76 mmol), and acetic acid (0.1 ml) were used to give 102.1 mg (0.31 mmol, 78.7% yield) of the title compound.

$^1$H NMR (400 MHz, CDCl$_3$) δ 8.04 (s, 1H), 7.96 (d, J=1.6 Hz, 1H), 7.84 (td, J=7.6, 1.8 Hz, 1H), 7.40-7.34 (m, 1H), 7.28-7.17 (m, 2H), 3.88 (d, J=7.2 Hz, 2H), 1.95-1.84 (m, 1H), 1.74-1.64 (m, 6H), 1.28-0.98 (m, 6H)

Compound 106: 7-(2-Fluorophenyl)-3-((1R,4R)-4-methylcyclohexyl)thieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1.0 ml), trans-4-methylcyclohexylamine (0.1 ml, 0.76 mmol), and acetic acid (0.1 ml) were used to give 87.1 mg (0.25 mmol, 63.6% yield) of the title compound.

$^1$H NMR (400 MHz, CDCl$_3$) δ 8.18 (s, 1H), 7.94 (d, J=1.6 Hz, 1H), 7.83 (td, J=7.6, 1.8 Hz, 1H), 7.39-7.33 (m, 1H), 7.27-7.16 (m, 2H), 4.89-4.81 (m, 1H), 2.05-2.01 (m, 2H), 1.91-1.87 (m, 2H), 1.73-1.63 (m, 2H), 1.55-1.43 (m, 1H), 1.30-1.20 (m, 2H), 0.97 (d, J=6.5 Hz, 3H)

Compound 107: 3-Cycloheptyl-7-phenylthieno[3,2-d]pyrimidin-4(3H)-one

In the same manner as the synthesis of Compound 1, methyl 3-amino-4-phenylthiophene-2-carboxylate (80 mg, 0.34 mmol), triethyl orthoformate (0.65 ml), cycloheptylamine (0.08 ml, 0.63 mmol), and acetic acid (0.08 ml) were used to give 103 mg (0.32 mmol, 93% yield) of the title compound.

$^1$H NMR (300 MHz, CDCl$_3$) δ 8.22 (s, 1H), 7.86-7.83 (m, 3H), 7.51-7.36 (m, 2H), 7.38-7.25 (m, 1H), 5.06-4.97 (m, 1H), 2.11-1.65 (m, 12H)

Compound 108: 3-Cycloheptyl-7-(2-fluorophenyl)thieno[3,2-d]pyrimidin -4(3H)-one In the same manner as the synthesis of Compound 1, methyl 3-amino-4-(2-fluorophenyl)thiophene-2-carboxylate (70 mg, 0.28 mmol), triethyl orthoformate (2 ml), cycloheptylamine (0.066 ml, 0.52 mmol), and acetic acid (0.1 ml) were used to give 45 mg (0.13 mmol, 47% yield) of the title compound.

$^1$H NMR (300 MHz, CDCl$_3$) δ 8.22 (s, 1H), 7.98 (s, 1H), 7.84-7.98 (m, 1H), 7.38-7.41 (m, 1H), 7.19-7.31 (m, 2H), 5.03 (m, 1H), 1.66-2.13 (m, 12H)

Compound 109: 3-(2,3-Dihydro-1H-inden-2-yl)-7-phenylthieno[3,2-d]pyrimidin-4(3H)-one In the same manner as the synthesis of Compound 1, methyl 3-amino-4-phenylthiophene-2-carboxylate (55.8 mg, 0.24 mmol), triethyl orthoformate (0.53 ml), 2-aminoindene (59.25 mg, 0.45 mmol), and acetic acid (0.06 ml) were used to give 48 mg (0.14 mmol, 58% yield) of the title compound.

$^1$H NMR (300 MHz, CDCl$_3$) δ 8.02 (s, 1H), 7.80 (s, 1H), 7.75-7.72 (m, 2H), 7.43 (t, J=10 Hz, 2H), 7.37-7.22 (m, 5H), 5.90-5.82 (m, 1H) 3.67 (d, J=10.4 Hz, 1H), 3.60 (d, J=10.4 Hz, 1H), 3.18 (dd, J=22.8, 4.4 Hz, 2H)

Compound 110: 3-(4-Isopropylcyclohexyl)-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1 ml), 4-isopropylcyclohexylamine (0.148 ml, 0.90 mmol), and acetic acid (0.1 ml) were used to give 88.5 mg (0.25 mmol, 58.4% yield) of the title compound.

$^1$H NMR (400 MHz, CDCl$_3$) δ 8.22 (s, 0.5H), 8.18 (s, 0.5H), 7.81-7.77 (m, 3H), 7.47-7.43 (m, 2H), 7.38-7.34 (m, 1H), 4.88-4.79 (m, 1H), 2.08-1.12 (m, 10H) 0.93 (d, J=6.6 Hz, 3H), 0.89 (d, J=6.8 Hz, 3H)

Compound 111: 7-Phenyl-3-(4-propylcyclohexyl)thieno[3,2-d]pyrimidin -4(3H)-one In the same manner as the synthesis of Compound 1, methyl 3-amino-4-phenylthiophene-2-carboxylate (100 mg, 0.43 mmol), triethyl orthoformate (1 ml), 4-propylcyclohexylamine (0.148 ml, 0.90 mmol), and acetic acid (0.1 ml) were used to give 105.7 mg (0.30 mmol, 69.7% yield) of the title compound.

$^1$H NMR (400 MHz, CDCl$_3$) δ 8.22 (s, 0.5H), 8.18 (s, 0.5H), 7.80-7.78 (m, 3H), 7.49-7.43 (m, 2H), 7.38-7.34 (m, 1H), 4.88-4.78 (m, 1H), 2.05-1.60 (m, 7H) 1.43-1.14 (m, 6H), 0.94-0.87 (m, 3H)

Compound 112: 3-(4-(Tert-butyl)cyclohexyl)-7-phenylthieno[3,2-d]pyrimidin-4(3H)-one In the same manner as the synthesis of Compound 1, methyl 3-amino-4-phenylthiophene-2-carboxylate (100 mg, 0.43 mmol), triethyl orthoformate (1 ml), 4-t-butylcyclohexylamine (0.161 ml, 0.90 mmol), and acetic acid (0.1 ml) were used to give 103.1 mg (0.28 mmol, 65.4% yield) of the title compound.

$^1$H NMR (400 MHz, CDCl$_3$) δ 8.51 (s, 0.5H), 8.20 (s, 0.5H), 7.82-7.80 (m, 3H), 7.50-7.45 (m, 2H), 7.41-7.36 (m, 1H), 5.05-5.01 (m, 0.5H), 4.88-4.80 (m, 0.5H), 2.22-1.94 (m, 4H) 1.80-1.60 (m, 2H), 1.41-1.10 (m, 3H), 0.90 (d, J=10 Hz, 9H)

Compound 113: (1r,4r)-4-(7-(2-fluorophenyl)-4-oxothieno[3,2-d]pyrimidin-3(4H)-yl)cyclohexyl acetate In the same manner as the synthesis of Compound 1, methyl 3-amino-4-(2-fluorophenyl)thiophene-2-carboxylate (100 mg, 0.40 mmol), triethyl orthoformate (1 ml), (1r,4r)-4-aminocyclohexyl acetate hydrochloride (147 mg, 0.76 mmol), and acetic acid (0.1 ml) were used to give 83.6 mg (0.22 mmol, 56.7% yield) of the title compound.

$^1$H NMR (400 MHz, CDCl$_3$) δ 8.14 (s, 1H), 7.95 (brd, J=1.3 Hz, 1H), 7.81 (td, J=1.7, 7.6 Hz, 1H), 7.39-7.33 (m, 1H), 7.27-7.16 (m, 2H), 4.94-4.86 (m, 1H), 4.82-4.74 (m, 1H), 2.20-2.06 (m, 7H) 1.86-1.76 (m, 2H), 1.71-1.61 (m, 2H)

Compound 114: 7-(2-Fluorophenyl)-3-isobutylthieno[3,2-d]pyrimidin-4(3H)-one

In the same manner as the synthesis of Compound 1, methyl 3-amino-4-(2-fluorophenyl)thiophene-2-carboxylate (100 mg, 0.40 mmol), triethyl orthoformate (1 ml), isobutylamine (0.076 ml, 0.76 mmol), and acetic acid (0.1 ml) were used to give 101 mg (0.33 mmol, 83.5% yield) of the title compound.

$^1$H NMR (400 MHz, CDCl$_3$) δ 8.05 (s, 1H), 7.96 (brd, J=1.6 Hz, 1H), 7.85 (td, J=1.8, 7.6 Hz, 1H), 7.40-7.34 (m, 1H), 7.28-7.17 (m, 2H), 3.87 (d, J=7.4 Hz, 2H), 2.30-2.16 (m, 1H), 0.99 (d, J=6.7 Hz, 6H)

Compound 115: 7-(2-Fluorophenyl)-3-neopentylthieno[3,2-d]pyrimidin-4(3H)-one In the same manner as the synthesis of Compound 1, methyl 3-amino-4-(2-fluorophenyl)thiophene-2-carboxylate (100 mg, 0.40 mmol), triethyl orthoformate (1 ml), neopentylamine (0.090 ml, 0.76 mmol), and acetic acid (0.1 ml) were used to give 96.5 mg (0.31 mmol, 76.3% yield) of the title compound.

$^1$H NMR (400 MHz, CDCl$_3$) δ 8.08 (s, 1H), 7.97 (brd, J=1.7 Hz, 1H), 7.86 (td, J=1.8, 7.6 Hz, 1H), 7.40-7.34 (m, 1H), 7.29-7.18 (m, 2H), 3.94 (s, 2H), 1.04 (s, 9H)

Compound 116: 3-Cyclooctyl-7-(o-tolyl)thieno[3,2-d]pyrimidin-4(3H)-one

In the same manner as the synthesis of Compound 1, methyl 3-amino-4-(o-tolyl)thiophene-2-carboxylate (100 mg, 0.40 mmol), triethyl orthoformate (1 ml), cyclooctylamine (0.107 ml, 0.77 mmol), and acetic acid (0.1 ml) were used to give 85.4 mg (0.24 mmol, 60.6% yield) of the title compound.

$^1$H NMR (300 MHz, CDCl$_3$) δ 8.11 (s, 1H), 7.63 (brd, J=0.8 Hz, 1H), 7.30-7.23 (m, 4H), 5.16-5.07 (m, 1H), 2.24 (s, 3H), 2.04-1.59 (m, 14H)

Compound 117: 3-Cycloheptyl-7-(o-tolyl)thieno[3,2-d]pyrimidin-4(3H)-one

In the same manner as the synthesis of Compound 1, methyl 3-amino-4-(o-tolyl)thiophene-2-carboxylate (100 mg, 0.40 mmol), triethyl orthoformate (1 ml), cycloheptylamine (0.098 ml, 0.77 mmol), and acetic acid (0.1 ml) were used to give 44 mg (0.13 mmol, 32.5% yield) of the title compound.

$^1$H NMR (400 MHz, CDCl$_3$) δ 8.12 (s, 1H), 7.63 (s, 1H), 7.34-7.24 (m, 4H), 5.01-4.96 (m, 1H), 2.24 (s, 3H), 2.11-2.06 (m, 2H), 1.90-1.59 (m, 10H)

Formulation Examples

The novel compounds of Formula 1 according to the present invention can be formulated into various dosage forms depending on the intended purpose. Some methods for preparing dosage forms containing the compounds of Formula 1 as active ingredients are exemplified below, but the present invention is not limited thereto.

Formulation Example 1

Tablets (Direct Compression)

5.0 mg of each of the active ingredients was sieved, mixed with 14.1 mg of lactose, 0.8 mg of Crospovidone USNF and 0.1 mg of magnesium stearate, and compressed into tablets.

Formulation Example 2

Tablets (Wet Granulation)

5.0 mg of each of the active ingredients was sieved and mixed with 16.0 mg of lactose and 4.0 mg of starch. To the mixture was added an appropriate amount of a solution of 0.3 mg of Polysolvate 80 in pure water, followed by atomization. After drying, the atomized mixture was sieved and mixed with 2.7 mg of colloidal silicon dioxide and 2.0 mg of magnesium stearate. The finely divided powder was compressed into tablets.

Formulation Example 3

Powders and Capsules 5.0 mg of each of the active ingredients was sieved and mixed with 14.8 g of lactose, 10.0 mg of polyvinyl pyrrolidone and 0.2 mg of magnesium stearate. The mixture was filled in a hard No. 5 gelatin capsule using a suitable device.

Formulation Example 4

Injectable Preparations 100 mg of each of the active ingredients, 180 mg of mannitol, 26 mg of Na$_2$HPO$_4$.12H$_2$O and 2974 mg of distilled water were mixed to prepare an injectable preparation.

The IC$_{50}$ values (nM) of the novel compounds of Formula 1 according to the present invention against mGluR1 were measured by the method described in the following experimental example.

Experimental Example 1 mGluR1 Activity Screening Method Using FDSS6000

Cells of Chem3 Cell Line (HTS145C:Millipore) in which mGluR1 was stably expressed were adjusted to a density of 2×10$^6$/ml. 50 μl of the cells were plated in each well of a 96-well plate, and stabilized at 5% $CO_2$ and 37° C. for 1 hr. The cells were allowed to react with an HBSS buffer containing a $Ca^{2+}$ fluorescent dye (FLIPR Calcium 5 assay kit: Molecular Devices) under the conditions of 5% $CO_2$ and 37° C. for 30 min. As a result of the reaction, the cells were labeled with the fluorescent dye. Separately from the 96-well plate containing the fluorescently labeled cells, another 96-well plate was prepared that contained L-Glutamate (final concentration=30 µM) activating mGluR1 and a blocking drug to be screened. Most cell-based HTS systems have liquid application systems necessary for drug injection but no liquid inhalation systems. For this reason, 25 µl of each of the blocking drug and L-Glutamate was prepared at a 6-fold higher concentration in an HBSS buffer and diluted 6-fold in the final volume (150 µl) of the cell plate before measurement. Specifically, after drug pretreatment for 75 sec following recording the reference value at 20 sec, a change in intracellular calcium concentration caused by L-glutamate administration was measured using FDSS6000. The inhibitory effect of the test substance was expressed as a percent (%) relative to the area of the 480 nm/520 nm ratio in a control group untreated with the test substance. 10 µM PCTC20001 was always used as the control drug.

For detailed imaging of calcium, the cells were selectively exposed to an excitation wavelength (480 nm) from four xenon light sources mounted in FDSS6000 through a computer-controlled filter wheel. Data were recorded at 1.23-sec intervals. Emitter fluorescence light entering through a 520 nm long-pass filter was allowed to pass through a cooled CCD camera mounted in the system. An average 480 nm/520 nm ratio was obtained in each well of the 96-well plate using a digital fluorescence analyzer. All imaging data were collected and analyzed with the help of a dedicated program for FDSS6000 (Hamamatsu Photonics).

Measurement of $IC_{50}$ Values Against mGluR1

The $IC_{50}$ values (nM) of the novel compounds of Formula 1 according to the present invention against mGluR1 are shown in Table 1.

TABLE 1

| Test compound | $IC_{50}$ (nM) |
| --- | --- |
| Compound 2 | 407 |
| Compound 6 | 58 |
| Compound 7 | 66 |
| Compound 18 | 112 |
| Compound 29 | 74 |
| Compound 32 | 30 |
| Compound 58 | 80 |
| Compound 59 | 661 |
| Compound 68 | 447 |
| Compound 69 | 1,987 |
| Compound 74 | 564 |

What is claimed is:

1. A compound represented by Formula 1:

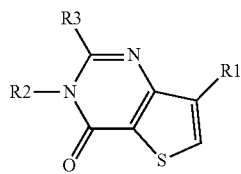

(1)

wherein R1 represents an aryl group, R2 represents an alkyl or aryl group, and R3 represents a hydrogen atom, an alkyl group, or an alkylamine group.

2. The compound or pharmaceutically acceptable salt thereof according to claim 1, wherein R1 is selected from substituted or unsubstituted phenyl, substituted or unsubstituted naphthalenyl, and substituted or unsubstituted benzodioxolyl; the substituted phenyl is phenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, substituted or unsubstituted stannyl, and phenyl; the substituted stannyl is alkylstannyl substituted with one to three $C_1$-$C_7$ alkyl groups; the substituted naphthalenyl is naphthalenyl in which some or all of the hydrogen atoms are replaced by substituents selected from halogen, $C_1$-$C_7$ alkyl, $C_1$-$C_7$ alkoxy, unsubstituted stannyl, $C_1$-$C_7$ alkylstannyl, $C_1$-$C_7$ dialkylstannyl, $C_1$-$C_7$ trialkylstannyl, and phenyl; and the substituted benzodioxolyl is benzodioxolyl in which some or all of the hydrogen atoms are replaced by substituents selected from halogen, $C_1$-$C_7$ alkyl, $C_1$-$C_7$ alkoxy, unsubstituted stannyl, $C_1$-$C_7$ alkylstannyl, $C_1$-$C_7$ dialkylstannyl, $C_1$-$C_7$ trialkylstannyl, and phenyl.

3. The compound or pharmaceutically acceptable salt thereof according to claim 1, wherein (i) R2 is selected from substituted or unsubstituted phenyl, substituted or unsubstituted benzonitrile, substituted or unsubstituted $C_1$-$C_7$ alkyl, allyl, vinyl, substituted or unsubstituted $C_3$-$C_{10}$ cycloalkyl, substituted or unsubstituted pyranyl, substituted or unsubstituted hydropyranyl, substituted or unsubstituted naphthalenyl, substituted or unsubstituted hydronaphthalenyl, substituted or unsubstituted furanyl, substituted or unsubstituted hydrofuranyl, substituted or unsubstituted piperidinyl, and substituted or unsubstituted $C_3$-$C_{10}$ heterocycloalkyl; or (ii) R2 has a $C_1$-$C_7$ alkyl group through which a group selected from substituted or unsubstituted phenyl, substituted or unsubstituted benzonitrile, substituted or unsubstituted $C_1$-$C_7$ alkyl, allyl, vinyl, substituted or unsubstituted $C_3$-$C_{10}$ cycloalkyl, substituted or unsubstituted pyranyl, substituted or unsubstituted hydropyranyl, substituted or unsubstituted naphthalenyl, substituted or unsubstituted hydronaphthalenyl, substituted or unsubstituted furanyl, substituted or unsubstituted hydrofuranyl, substituted or unsubstituted piperidinyl, and substituted or unsubstituted $C_3$-$C_{10}$ heterocycloalkyl is linked to the corresponding nitrogen atom of the thienopyrimidinone ring; the substituted phenyl is phenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the substituted benzonitrile is benzonitrile in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the substituted $C_1$-$C_7$ alkyl is $C_1$-$C_7$ alkyl in which one to three hydrogen atoms of the alkyl are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, allyl, $C_3$-$C_{10}$ cycloalkyl, furanyl, and hydrofuranyl; the substituted $C_3$-$C_{10}$ cycloalkyl is $C_3$-$C_{10}$ cycloalkyl substituted with substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, allyl, and $C_1$-$C_7$ alkyl; the substituted pyranyl is pyranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the hydropyranyl is dihydropyranyl or tetrahydropyranyl; the substituted hydropyranyl is hydropyranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the substituted naphthalenyl is naphthalenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the hydronaphthalenyl is selected from dihydronaphthalenyl, tetrahydronaphthalenyl, hexahydronaphthalenyl, and heptahydronaphthalenyl; the substituted hydronaphthalenyl is hydronaphthalenyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the substituted furanyl is furanyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the hydrofuranyl is dihydrofuranyl or tetrahydrofuranyl; the substituted hydrofuranyl is hydrofuranyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl; the substituted piperidinyl is (i) piperidinyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl, or (ii) piperidinyl in which a substituent selected from $C_1$-$C_7$ alkyl, halogenated $C_1$-$C_7$ alkyl, $C_1$-$C_7$ alkoxy, halogenated $C_1$-$C_7$ alkoxy, vinyl, and allyl is bonded to the nitrogen atom of the piperidine ring; the $C_3$-$C_{10}$ heterocycloalkyl is heterocycloalkyl in which one or two heteroatoms selected from N, O and S, and three to ten carbon atoms are bonded together to form a ring; and the substituted $C_3$-$C_{10}$ heterocycloalkyl is heterocycloalkyl in which some or all of the hydrogen atoms are replaced by substituents selected from halogen, $C_1$-$C_7$ alkyl, halogenated $C_1$-$C_7$ alkyl, $C_1$-$C_7$ alkoxy, halogenated $C_1$-$C_7$ alkoxy, hydroxy, nitro, vinyl, and allyl.

4. The compound or pharmaceutically acceptable salt thereof according to claim 1, wherein R3 is selected from hydrogen, $C_1$-$C_7$ alkyl, and substituted or unsubstituted amino, the substituted amino in R3 being amino substituted with one or two $C_1$-$C_7$ alkyl groups; and R3' is oxygen.

5. The compound or pharmaceutically acceptable salt thereof according to claim 1, wherein R1 is selected from phenyl, 2-fluorophenyl, 3-fluorophenyl, 4-fluorophenyl, 2-chlorophenyl, 3-chlorophenyl, 4-chlorophenyl, 2bromophenyl, 3-bromophenyl, 4-bromophenyl, 2-iodophenyl, 3-iodophenyl, 4-iodophenyl, 2-trimethylstannylphenyl, 3-trimethylstannylphenyl, 4-trimethylstannylphenyl, 2-methylphenyl, 3-methylphenyl, 4-methylphenyl, 2-methoxyphenyl, 3-methoxyphenyl, 4-methoxyphenyl, 3,4-dimethoxyphenyl, 4-benzodioxolyl, 5-benzodioxolyl, 1-naphthalenyl, and 2-naphthalenyl; R2 is selected from phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-methoxyphenyl, 3-methoxyphenyl, 4-methoxyphenyl, 3,4-dimethoxyphenyl, 3,5-dimethoxyphenyl, 2-hydroxyphenyl, 3-hydroxyphenyl, 4-hydroxyphenyl, 2-methylphenyl, 3-methylphenyl, 4-methylphenyl, 2,5-dimethylphenyl, 2,6-dimethylphenyl, 3,4-dimethylphenyl, benzonitrile, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-nitrophenyl, 3-nitrophenyl, 4-nitrophenyl, 2-vinylphenyl, 3-vinylphenyl, 4-vinylphenyl, butyl, allyl, cyclobutyl, cyclopentyl, cyclohexyl, cyclooctyl, cyclopropylmethyl, cyclohexylmethyl, 4-methylcyclohexyl, tetrahydropyran-4-yl, 1,2,3,4-tetrahydronaphthalen-1-yl, tetrahydrofuran-2-ylmethyl, 1-methylpiperidin-4-yl, isobutyl, neopentyl, 2-methylcyclohexyl, 3-methylcyclohexyl, 4-ethylcyclohexyl, and acetyloxy; and R3 is selected from hydrogen, methyl, and dimethylamino.

6. A compound or pharmaceutically acceptable salt thereof, wherein the compound is any one of the following compounds:

3,7-diphenylthieno[3,2-d]pyrimidin-4(3H)-one;
3-(2-fluorophenyl)-7-phenylthieno[3,2-d]pyrimidin-4(3H)-one;
3-(3-fluorophenyl)-7-phenylthieno[3,2-d]pyrimidin-4(3H)-one;
3-(4-fluorophenyl)-7-phenylthieno[3,2-d]pyrimidin-4(3H)-one;
3-(2-chlorophenyl)-7-phenylthieno[3,2-d]pyrimidin-4(3H)-one;
3-(3-chlorophenyl)-7-phenylthieno[3,2-d]pyrimidin-4(3H)-one;
3-(4-chlorophenyl)-7-phenylthieno[3,2-d]pyrimidin-4(3H)-one;
3-(3-bromophenyl)-7-phenylthieno[3,2-d]pyrimidin-4(3H)-one;
3-(4-bromophenyl)-7-phenylthieno[3,2-d]pyrimidin-4(3H)-one;
3-(2-methoxyphenyl)-7-phenylthieno[3,2-d]pyrimidin-4(3H)-one;
3-(3-methoxyphenyl)-7-phenylthieno[3,2-d]pyrimidin-4(3H)-one;
3-(4-methoxyphenyl)-7-phenylthieno[3,2-d]pyrimidin-4(3H)-one;
3-(3,4-dimethoxyphenyl)-7-phenylthieno[3,2-d]pyrimidin-4(3H)-one;
3-(3,5-dimethoxyphenyl)-7-phenylthieno[3,2-d]pyrimidin-4(3H)-one;
3-(4-hydroxyphenyl)-7-phenylthieno[3,2-d]pyrimidin-4(3H)-one;
7-phenyl-3-(o-tolyl)thieno[3,2-d]pyrimidin-4(3H)-one;
7-phenyl-3-(m-tolyl)thieno[3,2-d]pyrimidin-4(3H)-one;
7-phenyl-3-p-tolylthieno[3,2-d]pyrimidin-4(3H)-one;
3-(4-ethylphenyl)-7-phenylthieno[3,2-d]pyrimidin-4(3H)-one;
3-(2,6-dimethylphenyl)-7-phenylthieno[3,2-d]pyrimidin-4(3H)-one;
3-(2,5-dimethylphenyl)-7-phenylthieno[3,2-d]pyrimidin-4(3H)-one;
3-(3,4-dimethylphenyl)-7-phenylthieno[3,2-d]pyrimidin-4(3H)-one;
3-(4-oxo-7-phenylthieno[3,2-d]pyrimidin-3(4H)-yl)benzonitrile;
4-(4-oxo-7-phenylthieno[3,2-d]pyrimidin-3(4H)-yl)benzonitrile;
7-phenyl-3-(3-trifluoromethyl)phenyl)thieno[3,2-d]pyrimidin-4(3H)-one;
7-phenyl-3-(4-(trifluoromethyl)phenyl)thieno[3,2-d]pyrimidin-4(3H)-one;
7-phenyl-3-(4-trifluoromethoxy)phenyl)thieno[3,2-d]pyrimidin-4(3H)-one;
3-(4-nitrophenyl)-7-phenylthieno[3,2-d]pyrimidin-4(3H)-one;
7-phenyl-3-(3-vinylphenyl)thieno[3,2-d]-pyrimidin-4(3H)-one;
7-phenyl-3-(4-vinylphenyl)thieno[3,2-d]pyrimidin-4(3H)-one;
3-(4-fluorophenyl)-7-(2-fluorophenyl)thieno[3,2-d]pyrimidin-4(3H)-one;
3-(4-chlorophenyl)-7-(2-fluorophenyl)thieno[3,2-d]pyrimidin-4(3H)-one;

7-(2-fluorophenyl)-3-(4-methoxyphenyl)thieno[3,2-d]pyrimidin-4(3H)-one;
7-(2-fluorophenyl)-3-(4-hydroxyphenyl)thieno[3,2-d]pyrimidin-4(3H)-one;
7-(2-fluorophenyl)-3-(3-hydroxyphenyl)thieno[3,2-d]pyrimidin-4(3H)-one;
7-(2-fluorophenyl)-3-(m-tolyl)thieno[3,2-d]pyrimidin-4(3H)-one;
3-(3-chlorophenyl)-7-(2-fluorophenyl)thieno[3,2-d]pyrimidin-4(3H)-one;
7-(2-fluorophenyl)-3-(3-vinylphenyl)thieno[3,2-d]pyrimidin-4(3H)-one;
3-(7-(2-fluorophenyl)-4-oxothieno[3,2-d]pyrimidin-3(4H)-yl)benzonitrile;
3-(4-chlorophenyl)-7-(3-fluorophenyl)thieno[3,2-d]pyrimidin-4(3H)-one;
7-(3-fluorophenyl)-3-(4-methoxyphenyl)thieno[3,2-d]pyrimidin-4(3H)-one;
3-(4-chlorophenyl)-7-(4-fluorophenyl)thieno[3,2-d]pyrimidin-4(3H)-one;
7-(4-fluorophenyl)-3-(4-methoxyphenyl)thieno[3,2-d]pyrimidin-4(3H)-one;
7-(2-chlorophenyl)-3-(4-chlorophenyl)thieno[3,2-d]pyrimidin-4(3H)-one;
7-(2-chlorophenyl)-3-(4-methoxyphenyl)thieno[3,2-d]pyrimidin-4(3H)-one;
7-(3-chlorophenyl)-3-(4-chlorophenyl)thieno[3,2-d]pyrimidin-4(3H)-one;
7-(3-chlorophenyl)-3-(4-methoxyphenyl)thieno[3,2-d]pyrimidin-4(3H)-one;
3,7-bis(4-chlorophenyl)thieno[3,2-d]pyrimidin-4(3H)-one;
7-(4-chlorophenyl)-3-(4-methoxyphenyl)thieno[3,2-d]pyrimidin-4(3H)-one;
7-(2-bromophenyl)-3-(4-chlorophenyl)thieno[3,2-d]pyrimidin-4(3H)-one;
7-(2-bromophenyl)-3-(4-methoxyphenyl)thieno[3,2-d]pyrimidin-4(3H)-one;
7-(2-iodophenyl)-3-(4-methoxyphenyl)thieno[3,2-d]pyrimidin-4(3H)-one;
3-(4-methoxyphenyl)-7-(2-(trimethylstannyl)phenyl)thieno[3,2-d]pyrimidin-4(3H)-one;
3-(4-chlorophenyl)-7-(o-tolyl)thieno[3,2-d]pyrimidin-4(3H)-one;
3-(4-methoxyphenyl)-7-(o-tolyl)thieno[3,2-d]pyrimidin-4(3H)-one;
3-(4-chlorophenyl)-7-(m-tolyl)thieno[3,2-d]pyrimidin-4(3H)-one;
3-(4-methoxyphenyl)-7-(m-tolyl)thieno[3,2-d]pyrimidin-4(3H)-one;
3-(4-chlorophenyl)-7-(p-tolyl)thieno[3,2-d]pyrimidin-4(3H)-one;
3-(4-methoxyphenyl)-7-(p-tolyl)thieno[3,2-d]pyrimidin-4(3H)-one;
3-(4-chlorophenyl)-7-(2-methoxyphenyl)thieno[3,2-d]pyrimidin-4(3H)-one;
7-(2-methoxyphenyl)-3-(4-methoxyphenyl)thieno[3,2-d]pyrimidin-4(3H)-one;
3-(4-chlorophenyl)-7-(3-methoxyphenyl)thieno[3,2-d]pyrimidin-4(3H)-one;
7-(3-methoxyphenyl)-3-(4-methoxyphenyl)thieno[3,2-d]pyrimidin-4(3H)-one;
3-(4-chlorophenyl)-7-(4-methoxyphenyl)thieno[3,2-d]pyrimidin-4(3H)-one;
3,7-bis(4-methoxyphenyl)thieno[3,2-d]pyrimidin-4(3H)-one;
3-(4-chlorophenyl)-7-(3,4-dimethoxyphenyl)thieno[3,2-d]pyrimidin-4(3H)-one;
7-(3,4-dimethoxyphenyl)-3-(4-methoxyphenyl)thieno[3,2-d]pyrimidin-4(3H)-one;
7-(benzo[d][1,3]dioxol-5-yl)-3-(4-chlorophenyl)thieno[3,2-d]pyrimidin-4(3H)-one;
7-(benzo[d][1,3]dioxol-5-yl)-3-(4-methoxyphenyl)thieno[3,2-d]pyrimidin-4(3H)-one;
3-(4-chlorophenyl)-7-(naphthalen-1-yl)-3,4-dihydrothieno[3,2-d]pyrimidin-4(3H)-one;
3-(4-methoxyphenyl)-7-(naphthalen-1-yl)-3,4-dihydrothieno[3,2-d]pyrimidin-4(3H)-one;
3-(4-chlorophenyl)-7-(naphthalen-2-yl)-3,4-dihydrothieno[3,2-d]pyrimidin-4(3H)-one;
3-(4-methoxyphenyl)-7-(naphthalen-2-yl)-3,4-dihydrothieno[3,2-d]pyrimidin-4(3H)-one;
3-(4-methoxyphenyl)-2-methyl-7-phenylthieno[3,2-d]pyrimidin-4(3H)-one;
3-(4-chlorophenyl)-7-phenylthieno[3,2-d]pyrimidin-2,4(1H,3H)-dione;
3-(4-chlorophenyl)-2-(dimethylamino)-7-phenylthieno[3,2-d]pyrimidin-4(3H)-one;
3-butyl-7-phenylthieno[3,2-d]pyrimidin-4(3H)-one;
3-allyl-7-phenylthieno[3,2-d]pyrimidin-4(3H)-one;
3-cyclobutyl-7-phenylthieno[3,2-d]pyrimidin-4(3H)-one;
3-cyclopentyl-7-phenylthieno[3,2-d]pyrimidin-4(3H)-one;
3-cyclohexyl-7-phenylthieno[3,2-d]pyrimidin-4(3H)-one;
3-cyclooctyl-7-phenylthieno[3,2-d]pyrimidin-4(3H)-one;
3-(cyclopropylmethyl)-7-phenylthieno[3,2-d]pyrimidin-4(3H)-one;
3-(cyclohexylmethyl)-7-phenylthieno[3,2-d]pyrimidin-4(3H)-one;
3-((1R,4R)-4-methylcyclohexyl)-7-phenylthieno[3,2-d]pyrimidin-4(3H)-one;
7-phenyl-3-(tetrahydro-2H-pyran-4-yl)thieno[3,2-d]pyrimidin-4(3H)-one;
(R)-7-phenyl-3-(1,2,3,4-tetrahydronaphthalen-1-yl)thieno[3,2-d]pyrimidin-4(3H)-one;
(S)-7-phenyl-3-(1,2,3,4-tetrahydronaphthalen-1-yl)thieno[3,2-d]pyrimidin-4(3H)-one;
(S)-7-phenyl-3-((tetrahydrofuran-2-yl)methyl)thieno[3,2-d]pyrimidin-4(3H)-one;
(R)-7-phenyl-3-((tetrahydrofuran-2-yl)methyl)thieno[3,2-d]pyrimidin-4(3H)-one;
3-(1-methylpiperidin-4-yl)-7-phenylthieno[3,2-d]pyrimidin-4(3H)-one;
3-isobutyl-7-phenylthieno[3,2-d]pyrimidin-4(3H)-one;
3-neopentyl-7-phenylthieno[3,2-d]pyrimidin-4(3H)-one;
3-(2-methylcyclohexyl)-7-phenylthieno[3,2-d]pyrimidin-4(3H)-one;
3-(3-methylcyclohexyl)-7-phenylthieno[3,2-d]pyrimidin-4(3H)-one;
3-(4-ethylcyclohexyl)-7-phenylthieno[3,2-d]pyrimidin-4(3H)-one;
(1R,4R)-4-(4-oxo-7-phenylthieno[3,2-d]pyrimidin-3(4H)-yl)cyclohexyl acetate;
3-butyl-7-(2-fluorophenyl)thieno[3,2-d]pyrimidin-4(3H)-one;
3-allyl-7-(2-fluorophenyl)thieno[3,2-d]pyrimidin-4(3H)-one;
3-cyclobutyl-7-(2-fluorophenyl)thieno[3,2-d]pyrimidin-4(3H)-one;
3-cyclopentyl-7-(2-fluorophenyl)thieno[3,2-d]pyrimidin-4(3H)-one;

3-cyclohexyl-7-(2-fluorophenyl)thieno[3,2-d]pyrimidin-4(3H)-one;
3-cyclooctyl-7-(2-fluorophenyl)thieno[3,2-d]pyrimidin-4(3H)-one;
3-(cyclopropylmethyl)-7-(2-fluorophenyl)thieno[3,2-d]pyrimidin-4(3H)-one;
3-(cyclohexanemethyl)-7-(2-fluorophenyl)thieno[3,2-d]pyrimidin-4(3H)-one;
7-(2-fluorophenyl)-3-((1R,4R)-4-methylcyclohexyl)thieno[3,2-d]pyrimidin-4(3H)-one;
3-cycloheptyl-7-phenylthieno[3,2-d]pyrimidin-4(3H)-one;
3-cycloheptyl-7-(2-fluorophenyl)thieno[3,2-d]pyrimidin-4(3H)-one;
3-(2,3-dihydro-1H-inden-2-yl)-7-phenylthieno[3,2-d]pyrimidin-4(3H)-one;
3-(4-isopropylcyclohexyl)-7-phenylthieno[3,2-d]pyrimidin-4(3H)-one;
7-phenyl-3-(4-propylcyclohexyl)thieno[3,2-d]pyrimidin-4(3H)-one;
3-(4-(tert-butyl)cyclohexyl)-7-phenylthieno[3,2-d]pyrimidin-4(3H)-one;
(1r,4r)-4-(7-(2-fluorophenyl)-4-oxothieno[3,2-d]pyrimidin-3(4H)-yl)cyclohexyl acetate;
7-(2-fluorophenyl)-3-isobutylthieno[3,2-d]pyrimidin-4(3H)-one;
7-(2-fluorophenyl)-3-neopentylthieno[3,2-d]pyrimidin-4(3H)-one;
3-cyclooctyl-7-(o-tolyl)thieno[3,2-d]pyrimidin-4(3H)-one; and
3-cycloheptyl-7-(o-tolyl)thieno[3,2-d]pyrimidin-4(3H)-one.

7. A pharmaceutical composition for treating a brain disease, comprising the compound or pharmaceutically acceptable salt thereof according to claim 2 as an active ingredient.

8. A pharmaceutical composition for treating a brain disease, comprising the compound or pharmaceutically acceptable salt thereof according to claim 3 as an active ingredient.

9. A pharmaceutical composition for treating a brain disease, comprising the compound or pharmaceutically acceptable salt thereof according to claim 4 as an active ingredient.

10. A pharmaceutical composition for treating a brain disease, comprising the compound or pharmaceutically acceptable salt thereof according to claim 5 as an active ingredient.

11. A pharmaceutical composition for treating a brain disease, comprising the compound or pharmaceutically acceptable salt thereof according to claim 6 as an active ingredient.

12. A method for preparing the thienopyrimidinone derivative of Formula 1:

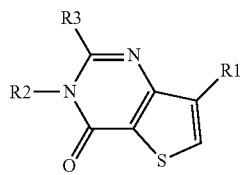

(1)

wherein R1 is selected from phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trimethylstannylphenyl, 3-trimethylstannylphenyl, 4-trimethylstannylphenyl, 2-methylphenyl, 3-methylphenyl, 4-methylphenyl, 2-methoxyphenyl, 3-methoxyphenyl, 4-methoxyphenyl, 3,4-dimethoxyphenyl, 4-benzodioxolyl, 5-benzodioxolyl, 1-naphthalenyl, and 2-naphthalenyl;

R2 is selected from phenyl, 2-fluorophenyl, 3-fluorophenyl, 4-fluorophenyl, 2-chlorophenyl, 3-chlorophenyl, 4-chlorophenyl, 2-bromophenyl, 3bromophenyl, 4-bromophenyl, 2-iodophenyl, 3-iodophenyl, 4-iodophenyl, 2-methoxyphenyl, 3-methoxyphenyl, 4-methoxyphenyl, 3,4-dimethoxyphenyl, 3,5-dimethoxyphenyl, 2-hydroxyphenyl, 3-hydroxyphenyl, 4-hydroxyphenyl, 2-methylphenyl, 3-methylphenyl, 4-methylphenyl, 2,5-dimethylphenyl, 2,6-dimethylphenyl, 3,4-dimethylphenyl, benzonitrile, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-nitrophenyl, 3-nitrophenyl, 4-nitrophenyl, 2-vinylphenyl, 3-vinylphenyl, 4-vinylphenyl, butyl, allyl, cyclobutyl, cyclopentyl, cyclohexyl, cyclooctyl, cyclopropylmethyl, cyclohexylmethyl, 4-methylcyclohexyl, tetrahydropyran-4-yl, 1,2,3,4-tetrahydronaphthalen-1-yl, tetrahydrofuran-2-ylmethyl, 1-methylpiperidin-4-yl, isobutyl, neopentyl, 2-methylcyclohexyl, 3-methylcyclohexyl, 4-ethylcyclohexyl, and acetyloxy; and R3 is selected from hydrogen, methyl, and dimethylamino, the method comprising:
(a) formylating an aryl acetonitrile 2 to afford an aryl hydroxyacrylonitrile 3;
(b) methylating the compound 3 to afford an aryl methoxyacrylonitrile 4;
(c) forming a thiophene ring from the aryl methoxyacrylonitrile to synthesize a thiophene derivative 5; and
(d) synthesizing the thienopyrimidinone derivative 1 from the thiophene derivative, as depicted in Reaction Scheme 1:

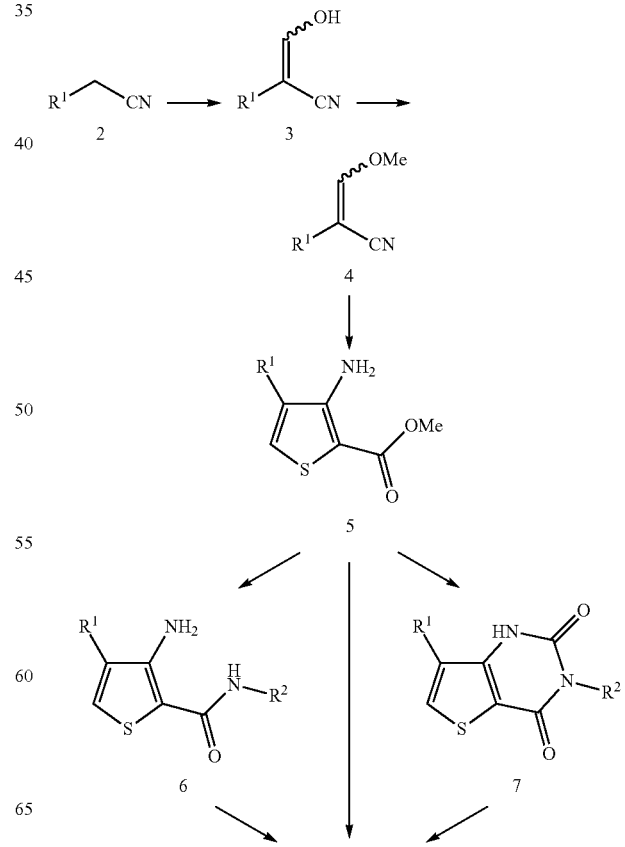

Reaction Scheme 1

-continued

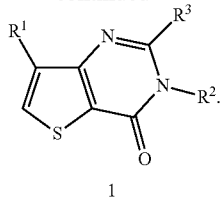

1

13. The method according to claim 12, wherein, in step (d), (i) the compound 1 is directly synthesized from the thiophene derivative, (ii) the thiophene derivative is amidated to synthesize a compound 6 and a pyrimidinone ring is formed to synthesize the compound 1, or (iii) the thiophene derivative is reacted with an isocyanate to synthesize a thienopyrimidinedione derivative 7 and an amine is introduced to prepare the compound 1.

* * * * *